United States Patent [19]
Goldman et al.

[11] Patent Number: 6,162,641
[45] Date of Patent: Dec. 19, 2000

[54] NEUREGULIN RESPONSE ELEMENT AND USES THEREFOR

[75] Inventors: Daniel Goldman, Ann Arbor, Mich.; Mohan K. Sapru, Naperville, Ill.

[73] Assignee: The Regents of the University of Michigan, Ann Arbor, Mich.

[21] Appl. No.: 09/092,636

[22] Filed: Jun. 5, 1998

Related U.S. Application Data

[60] Provisional application No. 60/048,847, Jun. 6, 1997.

[51] Int. Cl.[7] ............................ C12N 15/85; C12N 15/63; C07H 21/04
[52] U.S. Cl. ........................ 435/325; 536/24.1; 536/23.1; 435/320.1; 435/348; 435/349; 435/352; 435/363; 435/368; 435/371
[58] Field of Search ................................. 536/23.1, 24.1; 435/320.1, 325, 194, 455, 348, 349, 352, 363, 368, 371, 370.4

[56] References Cited

U.S. PATENT DOCUMENTS

| | | | |
|---|---|---|---|
| 4,708,716 | 11/1987 | Sibalis | 604/20 |
| 5,096,815 | 3/1992 | Ladner et al. | 435/69.1 |
| 5,233,409 | 8/1993 | Schwab | 356/402 |
| 5,237,056 | 8/1993 | Fischbach | 536/23.5 |
| 5,372,579 | 12/1994 | Sibalis | 604/20 |
| 5,403,484 | 4/1995 | Ladner et al. | 435/235.1 |

FOREIGN PATENT DOCUMENTS

| | | |
|---|---|---|
| WO 9206180 | 4/1992 | WIPO . |
| WO 9219749 | 11/1992 | WIPO . |
| WO 9220316 | 11/1992 | WIPO . |
| WO 9222635 | 12/1992 | WIPO . |
| WO 9304701 | 3/1993 | WIPO . |
| WO 9325234 | 12/1993 | WIPO . |
| WO 9406920 | 3/1994 | WIPO . |
| WO 9408007 | 4/1994 | WIPO . |
| WO 9411524 | 5/1994 | WIPO . |

OTHER PUBLICATIONS

Sapru, M. et al. "A 15–Base Pair Sequence Harboring a Putative ETS–Binding Site Confers Protein–Tyrosine Phosphatase, Neuregulin and RAS–Dependent Regulation of the Nicotinic Acetylcholine Receptor ε–Subunit Gene" 27th Annual Meeting of the Society for Neuroscience, Part 1, New Orleans, Louisiana, USA, Oct. 25–30, 1997. *Society for Neuroscience Abstracts* 23(1–2):391, Abstr. 157.10 (1997).

Sapru, M.K. et al. "Identification of a Neuregulin and Protein–Tyrosine Phosphatase Response Element in the Nicotinic Acetylcholine Receptor ε Subunit Gene: Regulatory Role of an Ets Transcription Factor" *Proc. Natl. Acad. Sci. USA* 95:1289–1294 (1998).

Si, J. et al. "Identification of an Element Required for Acetylcholine Receptor–Inducing Activity (ARIA)–Induced Expression of the Acetylcholine Receptor ε Subunit Gene" *The Journal of Biological Chemistry* 272(16):10367–10371 (1997).

Watson, D.K. et al. "Mammalian ets–1 and ets–2 Genes Encode Highly Conserved Proteins" *Proc. Natl. Acad. Sci. USA* 85:7862–7866 (1988).

Altiok, N. et al. "ErbB3 and ErbB2/neu Mediate the Effect of Heregulin on Acetylcholine Receptor Gene Expression in Muscle: Differential Expression at the Endplate" *Embo Journal* 14:4258–4266 (1995).

Bargmann, C.I. et al. "The Neu Oncogene Encodes an Epidermal Growth Factor Receptor–related Protein" *Nature* 319:226–230 (1986).

Chahine, K.G. et al. "A 102 Base Pair Sequence of the Nicotinic Acetylcholine Receptor Delta–subunit Gene Confers Regulation by Muscle Electrical Activity" *Development* 115:213–219 (1992).

Chu, G.C. et al. "Regulation of the Acetylcholine Receptor ε Subunit Gene by Recombinant ARIA: An In Vitro Model for Transynaptic Gene Regulation" *Neuron* 14:329–339 (1995).

Cristiano, R.J. et al. "Hepatic Gene Therapy: Adenovirus Enhancement of Receptor–mediated Gene Delivery and Expression in Primary Hepatocytes" *Proc. Natl. Acad. Sci. USA* 90:2122–2126 (1993).

Duclert, A. et al. "An 83–Nucleotide Promoter of the Acetylcholine Receptor ε–Subunit Gene Confers Preferential Synaptic Expression in Mouse Muscle" *Proc. Natl. Acad. Sci. USA* 90:3043–3047 (1993).

Duclert, A. et al. "Identification of an Element Crucial for the Sub–synaptic Expression of the Acetylcholine Receptor ε–Subunit Gene" *The Journal of Biological Chemistry* 27(29):17433–17438 (1996).

Egholm, M. et al. "PNA Hybridizes to Complementary Oligonucleotides Obeying the Watson–Crick Hydrogen–bonding Rules" *Nature* 365:566–568 (1993).

Egholm, M. et al. "Peptide Nucleic Acids (PNA). Oligonucleotide Analogues with an Achiral Peptide Backbone" *Journal of the American Chemical Society* 114:1895–1897 (1992).

Etienne–Julan, M. et al. "The Efficiency of Cell Targeting by Recombinant Retroviruses Depends on the Nature of the Receptor and the Composition of the Artificial Cell–Virus Linker" *Journal of General Virology* 73:3251–3255 (1992).

Falls, D.L. et al. "ARIA, a Protein That Stimulates Acetylcholine Receptor Synthesis, Is a Member of the Neu Ligand Family" *Cell* 72:801–815 (1993).

Goldman, D. et al. "Induction of Adult–type Nicotinic Acetylcholine Receptor Gene Expression in Noninnervated Regenerating Muscle" *Neuron* 7:649–658 (1991).

(List continued on next page.)

*Primary Examiner*—David Guzo
*Assistant Examiner*—Jon Shuman
*Attorney, Agent, or Firm*—Lahive & Cockfield LLP

[57] ABSTRACT

Methods for therapeutics and for screens are provided using a 15 bp sequence in the rat ε-subunit promoter that regulates PTPase, neuregulin and Ras-dependent gene expression. As this 15 bp sequence is necessary also for low ε-subunit gene expression in extrajunctional regions of the muscle fiber, the screens can identify agents that simultaneously and oppositely modulate expression in ε-subunit expression of synaptic and extrajunctional regions.

8 Claims, 8 Drawing Sheets

OTHER PUBLICATIONS

Goud, B. et al. "Antibody–mediated Binding of a Murine Ecotropic Moloney Retroviral Vector to Human Cells Allows Internalization But Not the Establishment of the Proviral State" *Virology* 163:251–254 (1988).

Hall, Z.W. and Sanes, J.R. "Synaptic Structure and Development: The Neuromuscular Junction" *Cell* 72(10 Suppl.):99–121 (1993).

Hawley, R.G. et al. "Versatile Retroviral Vectors for Potential Use in Gene Therapy" *Gene Therapy* 1:136–138 (1994).

Holmes et al. "Identification of Heregulin, a Specific Activator of p185$^{erbB2}$" *Science* 256:1205–1210 (1992).

Jo, S.A. et al. "Neuregulins are Concentrated at Nerve–muscle Synapses and Activate ACh–receptor Gene Expression" *Nature* 373:158–161 (1995).

Marchionni, M.A. et al. "Glial Growth Factors are Alternatively Spliced erbB2 Ligands Expressed in the Nervous System" *Nature* 362:312–318 (1993).

Martinou, J–C et al. "Acetylcholine Receptor–inducing Activity Stimulates Expression of the ε–Subunit Gene of the Muscle Acetylcholine Receptor" *Proc. Natl. Acad. Sci. USA* (1991).

Moacoso, L.M. et al. "Synapse–associated Expression of an Acetylcholine Receptor–inducing Protein, ARIA/Heregulin, and Its Putative Receptors, ErbB2 and ErbB3, in Developing Mammalian Muscle" *Developmental Biology* 172:158–169 (1995).

Mulligan, R.C. "The Basic Science of Gene Therapy" *Science* 260:926–932 (1993).

Neda, H. et al. "Chemical Modification of an Ecotropic Murine Leukemia Virus Results in Redirection of Its Target Cell Specificity" *The Journal of Biological Chemistry* 266(22):14143–14146 (1991).

Roux, P. et al. "A Versatile and Potentially General Approach to the Targeting of Specific Cell Types by Retroviruses: Application to the Infection of Human Cells by Means of Major Histocompatibility Complex Class I and Class II Antigens by Mouse Ecotropic Murine Leukemia Virus–Derived Viruses" *Proc. Natl. Acad. Sci. USA* 86:9079–9083 (1989).

Sapru, M.K. et al. "Protein–tyrosine Phosphatases Specifically Regulate Muscle Adult–type Nicotinic Acetylcholine Receptor Gene Expression" *The Journal of Biological Chemistry* 269(45):27811–27814 (1994).

Si, J. et al. "Identification of an Element Required for Acetylcholine Receptor–inducing Activity (ARIA)–induced Expression of the Acetylcholine Receptor ε Subunit Gene" *The Journal of Biological Chemistry* 272(16):10367–10371 (1997).

Wagner, E. et al. "Influenza Virus Hemagglutinin HA–2 N–Terminal Fusogenic Peptides Augment Gene Transfer by Transferrin–polylysine–DNA Complexes: Toward a Synthetic Virus–like Gene–transfer Vehicle" *Proc. Natl. Acad. Sci. USA* (1992).

Walke, W. et al. "Calcium–dependent Regulation of Rat and Chick Muscle Nicotinic Acetylcholine Receptor (nAChR) Gene Expression" *The Journal of Biological Chemistry* 269(30):19447–19456 (1994).

Wen, D. et al. "Neu Differentiation Factor: A Transmembrane Glycoprotein Containing and EGF Domain and an Immunoglobulin Homology Unit" *Cell* 69:559–572 (1992).

Yang, N–S. and Sun, W.H. "Gene Gun and Other Non–viral Approaches for Cancer Gene Therapy" *Nature Medicine* 1:481–483 (1995).

Zhu, X. et al. "Neuregulin Receptors, erbB3 and erbB4, are Localized at Neuromuscular Synapses" *Embo Journal* 14:5842–5848 (1995).

Ets2.pep Length:472 June2,1997 15:11 Type:p Check:9272..

```
  1 MNDFGIKNMD QVAPVANSFR GTLKRQPAFD TFDGSLFAVL PSLSEEQTLQ
 51 EVPTGLDSVS HDSATCELPL LTPCSKAVMS QALKATFSGF HKEQRRLGIP
101 KNPWLWNEQQ VCQWLHWATN EFSLVNVNLQ RFGMNGQMLC NLGKERFLEL
151 APDFVGDILW EHLEQMIKEN QEKTEDQYEE NSHLNAVPHW INSNTLGFGV
201 EQAPYGMQAP SYLKDGLLDG MCPPSATPAA LGSEQELQML PKSRLNTVSV
251 NYCSISQDFP GGNLNLLNSS SGKPKEHDSP ENGGDSFESS DSLLRSWNSQ
301 SSLLDVQRVP SFESFEEDCS QSLCLSKPTM SFKDYIQERS DPVEQGKPVI
351 PAAVLAGFTG SGPIQLWQFL LELLSDKSCQ SFISWTGDGW EFKLADPDEV
401 ARRWGKRKNK PKMNYEKLSR GLRYYYDKNI IHKTSGKRYV YRFVCDLQNL
451 LGFTPEELHA ILGVQPDTED *
```

FIG. 4

```
GAP of: Ets2.Pep  check: 9272  from:1 to: 472

TRANSLATE of: ets2.consensus check: 6408 from: 226 to: 1641
  generated symbols 1 to: 472.
    REVERSE-COMPLEMENT of: Ets2r.Consensus check: 3598 from: 1 to: 3619 to: Musets2.Pep check: 6892 from: 1 to: 469

TRANSLATE of: musets2.gb_ro check: 2157 from: 138 to: 1545
  generated symbols 1 to: 469.
  LOCUS       MUSETS2      1552 bp     mRNA             ROD       12-JUN-1993
  DEFINITION  Mouse erythroblastosis virus oncogene homolog 2 (ets-2) mRNA,
              complete cds.
  ACCESSION   J04103 . . .

Symbol comparison table: Gencoredisk:[Gcgcore.Data.Rundata]Blosum62.Cmp
  CompCheck: 6430

Gap Weight:       12       Average Match:     2.912
   Length Weight:        4       Average Mismatch: -2.003

Quality:   2376              Length:     472
            Ratio:  5.066                Gaps:       1
  Percent Similarity: 95.949   Percent Identity: 95.552

Match display thresholds for the alignment(s):
          | = IDENTITY
          : = 2
          . = 1
```

*FIG. 5*

```
Ets2.Pep x Musets2.Pep        June 2, 1997 15:26 ..

1 MNDFGIKNMDQVAPVANSFRGTLKRQPAFDTFDGSLFAVLPSLSEEQTLQ  50
    ||||||||||||||||||||||||||||||||||||||||||||:||||
  1 MNDFGIKNMDQVAPVANSFRGTLKRQPAFDTFDGSLFAVLPSLSEDQTLQ  50

51 EVPTGLDSVSHDSATCELPLLTPCSKAVMSQALKATFSGFHKEQRRLGIP 100
    |||||||||||||.||||||||||||||||||||||||| |||||||||
 51 EVPTGLDSVSHDSASCELPLLTPCSKAVMSQALKATFSGFQKEQRRLGIP 100

101 KNPWLWNEQQVCQWLHWQTNEFSLVNVNLQRFGMNGQMLCNLGKERFLEL 150
    ||||||.||||||||| |||||||||||||.||||||||||||||||||
101 KNPWLWSEQQVCQWLLWATNEFSLVNVNLHQFGMNGQMLCNLGKERFLEL 150

151 APDFVGDILWEHLEQMIKENQEKTEDQYEENSHLNAVPHWINSNTLGFGV 200
    ||||||||||||||||||||||||||||||||||||||||||||||| .
151 APDFVGDILWEHLEQMIKENQEKTEDQYEENSHLNAVPHWINSNTLGFSM 200

201 EQAPYGMQAPSYLKDGLLDGMCPPSATPAALGSEQELQMLPKSRLNTVSV 250
    |||||||||.| || ||| |||||||||||||  ||||||||||||.|
201 EQAPYGMQAPNYPKDNLLDSMCPPSATPAALGS..ELQMLPKSRLNTVNV 248

251 NYCSISQDFPGGNLNLLNSSSGKPKEHDSPENGGDSFESSDSLLRSWNSQ 300
    |||||||| |.||||..|||||:||||||||||||||||||||||||||
249 NYCSISQDFPSSNVNLLNNNSGKPKDHDSPENGGDSFESSDSLLRSWNSQ 298

301 SSLLDVQRVPSFESFEEDCSQSLCLSKPTMSFKDYIQERSDPVEQGKPVI 350
    |||||||||||||||||||||||||||·|||||||||||||||||||||
299 SSLLDVQRVPSFESFEEDCSQSLCLSKLTMSFKDYIQERSDPVEQGKPVI 348

351 PAAVLAGFTGSGPIQLWQFLLELLSDKSCQSFISWTGDGWEFKLADPDEV 400
    |||||||||||||||||||||||||||||||||||||||||||||||||
349 PAAVLAGFTGSGPIQLWQFLLELLSDKSCQSFISWTGDGWEFKLADPDEV 398

401 ARRWGKRKNKPKMNYEKLSRGLRYYYDKNIIHKTSGKRYVYRFVCDLQNL 450
    |||||||||||||||||||||||||||||||||||||||||||||||||
399 ARRWGKRKNKPKMNYEKLSRGLRYYYDKNIIHKTSGKRYVYRFVCDLQNL 448

451 LGFTPEELHAILGVQPDTED
    ||||||||||||||||||||
449 LGFTPEELHAILGVQPDTED
```

| | | | |
|---|---|---|---|
| Mouse | TAGGTGACAGTCCC | CAAACCTAGCCCCGGA | ACTAACACCCTCCTCC |
| Human | TAGGTGACAGTCCC | CTAAC--AGCCCCGGA | ACTAACACCCTCCTCC |
| Rat | TAGGTGACAGTCCC | TAAACCTAGTCCGGA | ACTAGCACCCTCCTCC |

*FIG. 7*

NEUREGULIN RESPONSE ELEMENT AND USES THEREFOR

RELATED APPLICATION

This application claims the benefit of priority under 35 U.S.C. 19(e) to co-pending U.S. Provisional application Ser. No. 60/048,847, filed Jun. 6, 1997, entitled "Neuregulin Response Element and Uses Therefor" the entire contents of which are hereby incorporated by reference.

GOVERNMENT FUNDING

Work described herein was supported in part by finding from the National Institutes of Health. The United States Government may have certain rights in the invention.

BACKGROUND

Synapse formation and subsequent maturation involves complex interactions between the presynaptic cell and its postsynaptic target. As a model synapse, the neuromuscular junction (NMJ) provides a relatively simple system to study molecular mechanisms mediating some of these interactions. At this synapse, synaptic transmission between the motor neuron and its target muscle fiber is mediated by the muscle nicotinic acetylcholine receptor (nAChR), a multi-subunit ligand-gated ion channel (Hall, Z. W., and Sanes, J. R. (1993) Cell 10 (Suppl.) 99–121).

During the development of the neuromuscular synapse, nerve-evoked muscle activity suppresses expression of embryonic-type nAChR ($\alpha_2\beta\gamma\delta$) throughout the muscle fiber (Hall, Z. W., and Sanes, J. R. (1993) Cell 10 (Suppl.) 99–121; Goldman, D., et al. (1988) Neuron 1, 329–333) while muscle innervation induces expression of adult-type nAChRs ($\alpha_2\beta\epsilon\delta$) at the endplate. This spatially restricted expression of adult-type nAChRs is largely a result of selective induction of the genes encoding these subunits in endplate-associated myonuclei (Hall, Z. W., et al. (1993) Cell 10 (Suppl.) 99–121). The transcriptional mechanisms by which the motor neuron regulates gene expression in these subsynaptic nuclei are not well understood.

Protein-tyrosine phosphatase (PTPase) activity selectively suppresses muscle adult-type nAChR genes. Changes in protein tyrosine phosphorylation have been proposed to contribute to synapse-specific gene expression (Sapru, M. K., et al. (1994) J. Biol. Chem. 269, 27811–27814). Neuregulins are motor neuron-derived factors that function as ligands for EGF receptor-related (erbB) tyrosine kinases and stimulate adult-type nAChR synthesis (Bargmann, C. I., et al. (1986) Nature 319, 226–230; Falls, D. L., et al. (1993) Cell 72, 801–815; Martinou, J. C., et al. (1991) Proc. Natl. Acad. Sci. USA 88, 7669–7673; Marchionni, M. A., et al. (1993) Nature 362, 312–317; Altiok, N., et al. (1995) EMBO J. 14, 4258–4266; Jo, S. A., et al. (1995) Nature 373, 158–161; Zhu, X. J., et al. (1995) EMBO J. 14, 5842–5848; Chu, G. C., et al. (1995) Neuron 14, 329–339). Neuregulins include neu differentiation factor, heregulin, glial growth factor, and acetylcholine receptor inducing activity (ARIA), which are alternatively spliced products of a single gene (Marchionni, M. A., et al. (1993) Nature 362, 312–317; U.S. Pat. No. 5,237,056; WO 94/08007). Whether the neuregulin signaling pathway differs from that perturbed by PTPase overexpression is not known.

Since the $\epsilon$-subunit gene is unique to adult-type nAChRs and is locally expressed at the endplate, it serves as a marker for regulatory mechanisms involved in synapse-specific expression. In addition, this gene is most sensitive to neuregulin induction (Martinou, J. C., et al. (1991) Proc. Natl. Acad. Sci. USA 88, 7669–7673). Si et al. (Si., J. et al. (1997) J. Biol. Chem. 272:10, 367–10, 371) have recently identified a 10 nucleotide element in the mouse $\epsilon$-subunit promoter (−55 to −46 upstream of the start site of transcription in the mouse) that is responsive to ARIA (ARE). It shares no significant identity with the NRE of the present invention, and is approximately 50 nucleotides from the 5' end of a mouse sequence that is identical to rat NRE in 13 of 15 nucleotides. However, a regulatory element in the $\epsilon$-promoter conferring responsiveness to neuregulin, responsiveness to activated Ras, and responsiveness to PTPase has not been identified.

SUMMARY OF THE INVENTION

The present invention relates to a nucleic acid comprising an neuregulin response element (NRE) and its therapeutic applications and uses in methods for drug screening. Transcription modulated by the presence upstream of an NRE sequence directs gene product expression to a neuromuscular synapse, and represses gene product expression at extrajunctional sites.

As herein defined an NRE is a DNA sequence regulatory element which mediates one or more of the following functions: a positive transcriptional response to the presence of a neuregulin; a positive transcriptional response to the presence of activated Ras, and a negative transcriptional response to the presence of a dual specificity PTPase. In a preferred embodiment, an NRE comprises all or a portion of the nucleotide sequence 5' TAAACCTAGT CCGGA 3' (SEQ ID No. 3) which correspond to nucleotides −55 to −69 (starting from the transcription start site) of the gene for the $\epsilon$-subunit of nAChR in the rat as shown in FIG. 7, or the functional equivalent thereof.

In one aspect, the invention provides an NRE which is a homolog of the rat nAChR $\epsilon$-subunit, for example an NRE sequence derived from the genome of another mammal, such as a human or a mouse. In another aspect, the invention provides an NRE which differs from the sequence shown in SEQ ID No. 3 by mutation, including but not limited to, mutations of one or more nucleotides by substitution (including both transitions and transversions), deletion, or addition, provided that the mutation does not eliminate NRE function as defined herein. For example, the NRE nucleotide sequence can be at least about 70%, by 80%, or by 90% homologous to the nucleotide sequence shown in SEQ ID No. 3. In one embodiment, the NRE is a naturally-occurring polymorphic variant of the rat NRE defined by SEQ ID No. 3.

NREs of the present invention can be isolated from the promoter region of a gene (e.g., a gene encoding an nAChR $\epsilon$-subunit). Alternatively, an NRE can be obtained by site-directed mutagenesis of, for example, the NRE of rat nAChR $\epsilon$-subunit. Alternatively, an NRE may be chemically synthesized de novo. More than one NRE may be used in a construct, for example in a direct repeat in a promoter region to induce even greater transcriptional regulation in an NRE-dependent manner, or separately on a construct carrying more than one heterologous gene, each gene with at least one NRE in its promoter region. The term "NRE-dependent" means transcription of a gene which is dependent on or affected by (e.g., upregulated or downregulated) the presence of an NRE as defined herein operably linked to the gene.

In another aspect, the invention features an isolated nucleic acid comprising an neuregulin response element (NRE) derived from a contiguous promoter sequence existing in a naturally occurring genome of an organism from which the NRE is derived, wherein the NRE is operably linked in an expression vector so that it regulates a heterologous gene. The nucleic acid in a preferred embodiment of the invention is DNA. The recombinant expression can be introduced into a host cell under conditions such that the expression of the heterologous gene of interest is regulated in an NRE-dependent manner in the recombinant cell.

The invention features also isolated nucleic acids comprising an NRE, wherein the ability of the NRE to modulate a heterologous gene is affected by an agent selected from the group consisting of: a protein of the neuregulin family, an activated Ras protein, and a dual specificity PTPase. In one embodiment, the isolated nucleic acid comprises an NRE having all or a portion of the nucleotide sequence shown in SEQ ID No. 3, or a functional equivalent thereof. For example, an NRE may comprise a nucleotide sequence which differs from all or a portion of the sequence of SEQ ID No. 3 by e.g., four or fewer nucleotides, and is capable of modulating expression of an operably linked gene under the regulation of a protein of the neuregulin family, an activated Ras protein, or a dual specificity protein phosphatase. Alternatively, an NRE may be at least about 70, 80 or 90% homologous to all or a portion of the nucleotide sequence shown in SEQ ID No. 3, and is capable of modulating expression of an operably linked gene under the regulation of a protein of the neuregulin family, an activated Ras protein, or a dual specificity protein phosphatase.

An "isolated" NRE is isolated from its natural sequence context but may include one or more nucleotides which naturally flank the NRE (e.g., sequences located at the 5' and 3' ends of the NRE) in the genome of the organism from which the NRE is isolated. For example, an isolated NRE may be characterized by the formula 5' N1-X-N2 3', wherein X is an NRE as defined herein, N1 is equal to or less than 30 bp of the naturally occurring 5' flanking region of the NRE, and N2 is equal to or less than 60 bp of the naturally occurring 31 flanking region of the NRE.

The invention further provides recombinant expression vector comprising a heterologous gene of interest operably linked to the NRE, and also a host cell transfected with the expression vector. The host cell can be a worm cell, an insect cell, a fish cell, an avian cell or a mammalian cell. Preferably the host cell is a nerve cell or a muscle cell.

In yet another embodiment, the invention provides comprises a method for expressing a heterologous gene of interest in a cell which involves choosing the heterologous gene to be expressed; constructing a DNA molecule comprising the gene to be expressed, operably linked to an NRE; inserting the DNA molecule into a recombinant expression vector; and introducing the recombinant expression vector into a host cell under conditions such that the expression of the heterologous gene of interest is regulated in an NRE-dependent manner in the cell. In this method, the heterologous gene can be, for example, a reporter gene, which can be chosen from, but is not limited to, the group consisting of chloramphenicol acetyl transferase, β-galactosidase, luciferase, horseradish peroxidase and alkaline phosphatase. These methods provide for the user of the invention to have the gene encoding the protein to have functional activity at a synapse. Genes included among those that are desirable to express at a synapse include agrin, laminin β-2, dystroglycan, rapsyn, utrophin or MuSK. The method of contacting a host cell with the construct can be used to introduce the recombinant expression vector into the cell in vivo, or ex vivo, and in the latter case, the recombinant cell can be introduced into a subject to permit in vivo expression of the heterologous gene.

In still yet another aspect, the invention provides a method for directing gene expression to the neuromuscular junction, this term used herein interchangeably with the term synapse and the term junctional endplate. This method involves choosing a heterologous gene to be expressed; constructing a DNA molecule comprising the gene to be expressed, operably linked to an neuregulin response element (NRE); inserting the nucleic acid molecule into a recombinant expression vector; and contacting a recipient cell with the recombinant expression vector in vivo, so that expression of the heterologous gene is directed to the neuromuscular junction. The method has therapeutic application if the recipient cell is from a subject having a transynaptic expression disorder, for example, having myasthenia gravis, familial infantile myasthenia, acetylcholinesterase deficiency, slow channel syndrome or AChR deficiency. The method also has therapeutic application if the recipient cell is from a subject having a condition such as a neurological degenerative disease, a muscular degenerative disease, damage to a spinal cord, damage to a peripheral nerve, damage to a skeletal muscle tissue or damage to a brain tissue.

As used herein, the terms "transynaptic region", "neuromuscular junction", and "synaptic region", all refer the same subcellular location at the junction of a nerve and a muscle cell. Desirable genes for targeting to this subcellular location include but are not limited to genes encoding neurotrophic factors, such as BDNF, CNTF, NGF, NT-3 or NT-4/5. Alternatively, the gene may encode a protein having functional activity at a synapse, for example, agrin, laminin β2, dystroglycan, rapsyn, utrophin and MuSK.

In another aspect, the invention features a method for identifying an agent able to regulate synaptic-specific gene transcription from among a group of candidate compounds. This method includes the steps of constructing a DNA molecule which comprises a reporter gene operably linked to an NRE (neuregulin response element); inserting the DNA molecule into a recombinant expression vector; introducing the recombinant expression vector into a host cell; exposing the host cell to a candidate compound; measuring the reporter gene activity in the presence of said candidate compound; and comparing the reporter gene activity in the presence of said compound with the activity in the absence of said compound, to determine whether said candidate compound is an agent capable of regulating synaptic-specific transcription of a gene operably linked to an NRE.

The methods of the invention further include a method for identifying an agent which modulates neuregulin-dependent transynaptic-specific gene transcription from among a group of candidate compounds. In one embodiment, the comprising the steps of constructing a DNA molecule which comprises a reporter gene operably linked to an NRE (neuregulin response element); inserting the DNA molecule into a recombinant expression vector; introducing the recombinant expression vector into a host cell; supplying the host cell with an amount of a neuregulin sufficient to induce neuregulin-dependent gene transcription; exposing the host cell to a candidate compound; measuring the reporter gene activity in the presence of said candidate compound; and comparing the reporter gene activity in the presence of said compound with the activity in the absence of said compound as an indication of whether said compound is an agent capable of regulating synapse-specific transcription of a gene operably linked to the NRE. For this method, a species of neuregulin to add to the cells can be heregulin, ARIA, NDF or GGF.

The invention also features a method for identifying an agent which modulates synapse-specific gene transcription, from among a group of candidate compounds, involving the steps of constructing a DNA molecule which comprises a reporter gene operably linked to an NRE (neuregulin response element); constructing a DNA molecule which comprises a gene encoding a dual specificity protein phosphatase; inserting said DNA molecules into a recombinant expression vector either together or separately; introducing the recombinant expression vector into a host cell; contacting the host cell with a candidate compound; measuring the reporter gene activity in the presence of said compound; and comparing the reporter gene activity in the presence of said compound with the activity in the absence of said compound as an indication of whether said compound is capable of regulating synapse-specific expression by modulating transcription of a gene operably linked to an NRE. In this method, the dual specificity protein phosphatase can be CL100.

In another aspect, the invention provides an NRE-binding protein comprising an amino acid sequence having at least about 95% homology to the amino acid sequence shown in SEQ ID No. 4. The term "NRE-binding protein" means a protein which binds to an NRE as defined herein thereby effecting NRE-mediated (e.g., in an NRE-dependent manner) gene transcription. In one embodiment, the NRE-binding protein comprises the amino acid sequence shown in SEQ ID No. 4.

BRIEF DESCRIPTION OF THE DRAWINGS

FIG. 4 is an amino acid sequence (SEQ ID No. 4) of rat Ets-2 protein, deduced from the DNA sequence of a gene cloned from a phage ( cDNA library prepared from Rattus norvegicus skeletal muscle; the one-letter system of designating each amino acid is used.

FIG. 5 shows a comparison of the amino acid sequences of the Ets-2 protein from rat (top) (SEQ ID NO:4) and from mouse (bottom) (SEQ ID NO:9); identical residues are indicated by a vertical line joining the top and bottom sequences; a difference at a residue in which the amino acids of the two proteins are similar chemically, such as aspartic acid (D) and glutamic acid (E) are indicated by two dots joining the sequences; other less similar amino acids that are different for the two proteins, for example histidine (H) and glutamine (Q) are indicated by one dot; different amino acids with chemical dissimilarity, for example leucine (L) and proline (P), are indicated by a blank; residues lacking in one sequence in comparison to the other are indicated by a dot in the sequence, for example, between mouse residues 233 and 234.

FIG. 7 shows the nucleotide sequences of the mouse, human, and rat NREs, with additional flanking 5' and 3' nucleotides of each. The NRE is indicated set off in the middle of the sequences, separated from flanking sequences by spaces. The rat NRE sequence (accession number GB|L19594, identified in the context of the sequence published in Walke, W. et al., (1994) J. Biol. Chem. 269:19447–19456) is also shown in SEQ ID No. 3, and corresponds to nucleotides at positions –83 to –39 with respect to the start site of transcription. The mouse sequence, accession number GB|S58221, corresponds to nucleotides at positions –36 to +10 with respect to the start site of transcription (Duclert, A. et al.((1993) Proc. Natl. Acad. Sci. USA 90:3043–3047; Duclert, A. et al. (1996) J. Biol. Chem. 271, 17433–17438). The human sequence, accession number EMB Z84811, corresponds to base counts 1456 to 1498 of the sequence provided, described as a sequence concerning transcriptional control of human muscle nicotinic acetylcholine receptor. The figure shows that two nucleotides differ by substitution in the NRE of mouse, and two by deletion in the NRE of human, in comparison to that of rat.

DETAILED DESCRIPTION

Figure 1:
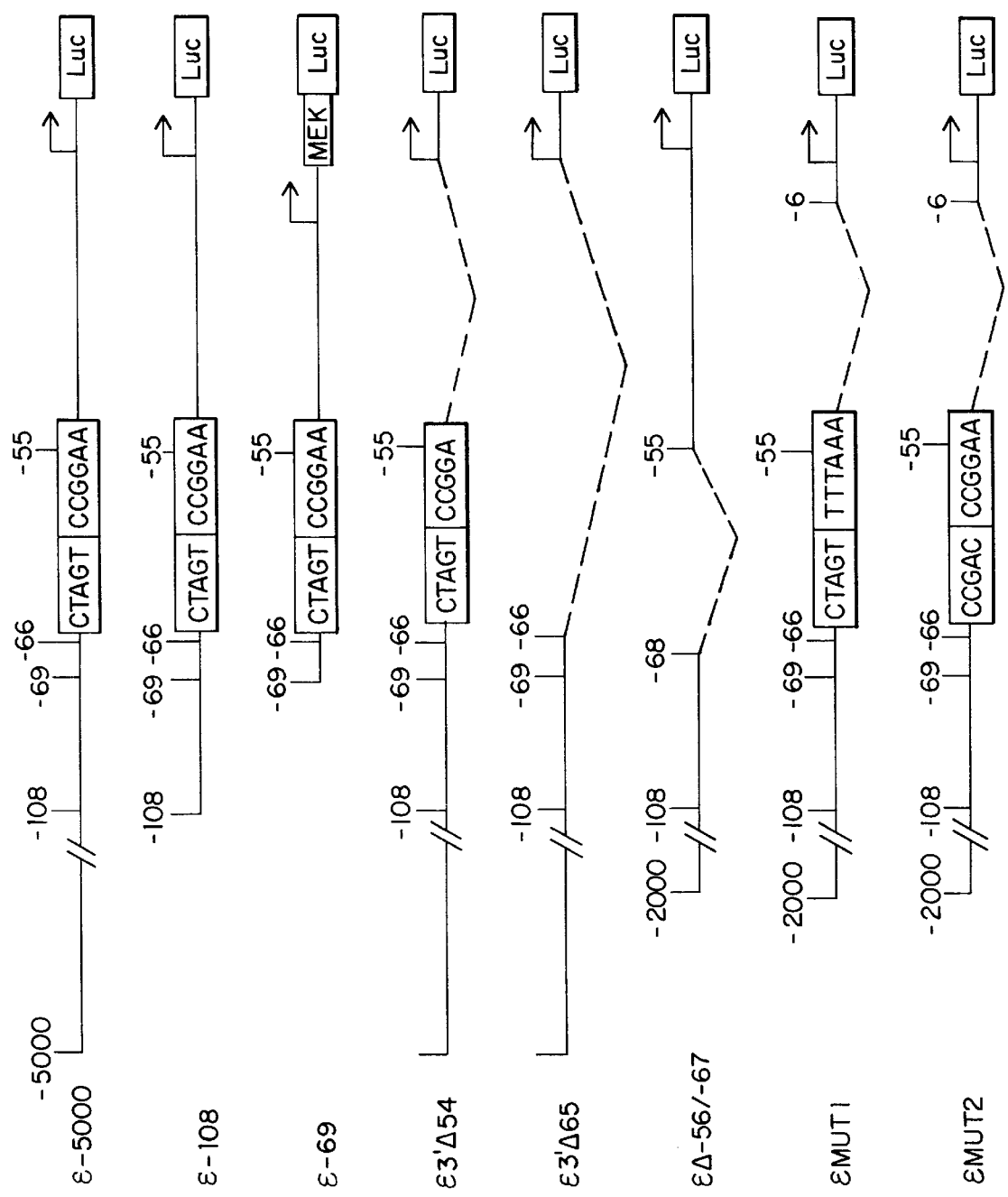
FIG. 1 shows genetic constructs for expression of rat ε-subunit promoter, in which expression of the luciferase (Luc) structural gene is driven either by a wild-type ε-subunit promoter (ε–5000) or various 5' (ε–108, ε–69) and 3' (ε3'Δ54, ε2'Δ65) deletion mutants, or an internal deletion mutant, εΔ–56/–67; dotted lines represent deleted DNA in particular mutants; mutations 1 and 2 respectively represent constructs in which site-directed mutagenesis of wild-type nucleotides CCGG (positions between –59 and –56) has been used to change these nucleotides to TTTA (εMUT1), and wild-type nucleotides TAGT (positions between –63 and –60) to CGAC (εMUT2), respectively (SEQ ID NOs:5, 6,7, and 8); the transcriptional start site is indicated by an arrow.

The present invention relates to methods and compositions with therapeutic or drug-screening applications of a 15 base pair (bp) sequence derived from the promoter of the ε-subunit of the nAChR. More specifically, this application relates to methods of localization of expression of protein, encoded by genes operatively linked to this 15 bp sequence, to the NMJs of cells of nerve and muscle origin, and to suppression of expression at extrajunctional locations. The present invention further concerns providing screens as tools to obtain drugs that can modulate this expression under a range of conditions of presence of one or more proteins in the family known as neuregulins, and state of phosphorylation of the Ras signal transduction cascade, including phosphorylation of Ras protein.

One aspect of the present invention provides a method for obtaining expression at a neuromuscular junction (NMJ) of a protein encoded by a gene, in a cell of a subject in need of the protein, comprising contacting a cell of that subject with a nucleic acid comprising at least the gene encoding the protein, operably linked to nucleic acid comprising the neuregulin-PTPase-Ras sensitive nAChR ε-subunit regulatory element, to produce a genetically transformed cell, which expresses the protein encoded by the gene at the NMJ. In one embodiment, the method can include a step in which the cell is contacted in the subject in vivo. In this embodiment, it is preferably that the cell is in muscle tissue, or is a nerve cell. Further, the muscle tissue can be skeletal muscle or cardiac muscle, and the nerve cell can be in the central nervous system or can be a peripheral nerve. Further, the nucleic acid that is operably linked to the regulatory element encodes two or more proteins. The genes encoding these proteins can be carried on the same vector, or on two or more similar or unlike vectors, each gene being provided with the regulatory E-promoter sequence operably linked to that gene. In a preferred embodiment, an antibiotic or drug such as G418 is used to select for uptake of the vector.

In another embodiment, the method can include a step in which the cell is contacted ex vivo and then delivered to the subject. The cell that is contacted with the nucleic acid can be obtained from a heterologous donor, or it can be obtained from the subject cells contacted with nucleic acid ex vivo in cell culture, prior to, concurrent with, or after treatment with nucleic acid. The cell can be treated with a neuregulin ex vivo, or after return to the subject, or neuregulin can be administered both to cells in culture and to the subject after the subject has been the recipient of cells delivered in vivo. In a preferred embodiment, an antibiotic or drug such as G418 is used to select for uptake of the vector.

Another aspect of the present invention features the DNA sequence of the nAChR neuregulin-PTPase-Ras regulatory element, the nucleotide sequence being 5' TAAAC-CTAGTCCGGA 3' (SEQ ID No. 3) as read on the strand carrying the protein coding sequence. In the genome, this nucleotide sequence is located upstream, to the 5' direction as encoded by the nucleic acid, of the transcription initiation site of the gene encoding the nAChR ε-subunit. This sequence is here given the name "neuregulin response element" or NRE.

In a preferred embodiment, the NRE comprises nucleotides −55 to −69 upstream of the transcription initiation site of the gene encoding the nAChR ε-subunit in the rat. In other embodiments, the nucleotide sequence differs from SEQ ID No. 3 by four or fewer nucleotides, so is at least 70% identical, is at least 80% identical, or is at least 90% identical to SEQ ID No. 3. In yet other embodiments, the sequence of the NRE for antisense applications is at least 70% identical to the complement of SEQ ID No. 3, is at least 80% identical to the complement of SEQ ID No. 3, or is at least 90% identical to the complement of SEQ ID No. 3.

In another aspect, the subject of the therapeutic methods of the present invention is a mammal, more preferably, the subject is an equine, bovine, ovine, porcine, caprine, rodent, primate, or higher ape, and most preferably, the subject is a human patient.

In another aspect, the expression of the protein at the NMJ is induced in cells that are used for a drug screen, or for a therapeutic application of ex vivo cells, by addition of a neuregulin to the medium. In a preferred embodiment, the neuregulin is heregulin. In other embodiments, the neuregulin is heregulin, ARIA, NDF or GGF.

In a preferred embodiment for therapy in cases in which muscle or nerve tissue regeneration in a subject is the objective, the NRE is operatively linked to a gene encoding a neurotropic or neurotrophic factor, for example, BDNF, CNTF, GNF, NGF, N8-3, NT-4/5, or GGF, or to any of other factors known in the art that have been identified to enhance nerve and muscle cell growth and proliferation. In a particularly preferred embodiment, the NRE is operatively linked to a gene encoding a protein that enhances formation of a neuromuscular synapse, for example, rapsyn, utrophin, laminin β−2, dystroglycan, MuSK, and agrin and similar components of synapses in nerve and muscle tissue.

An objective of the invention is to provide remediation of a transynaptic expression deficiency (TSED), so that a patient suffering with a TSED condition in which insufficient amounts of a protein are expressed at a NMJ can be treated by the methods and compositions herein. TSED can be remediated by synapse-specific expression, induced by administration of a neuregulin, of a gene under regulation of the NRE provided in the present invention. TSED remediation is not limited to providing expression of one or more of the proteins listed herein; nor is remediation limited to providing the particular deficient protein. Rather, the methods and compositions of the invention can be used to induce junctional-specific expression of appropriate additional growth factors, structural proteins, alternative receptor subunits to those that are defective or deficient, and other proteins that contribute to development of a functional neuromuscular synapse.

In a particularly preferred embodiment, the therapeutic compositions and methods of the invention are used to treat a subject who is a patient with an adult or juvenile form of myasthenia gravis. These diseases include familial infantile myasthenia gravis, acetylcholinesterase deficiency, slow channel syndrome, and AChR deficiency. In other preferred embodiments, the subject is a patient with a degenerative neurological or muscular disease, for example the subject is a patient with Alzheimer's disease. In other embodiments, the subject is a patient in need of regeneration of muscle or nerve tissue, for example, a patient with spinal cord or peripheral nerve damage.

In another preferred embodiment, the patient has had loss of brain tissue. Such patients include those who have experienced a stroke, brain aneurysm, brain infection, brain tumor, brain bleeding or brain blood clot.

In another aspect, the present invention provides therapeutic methods and compositions consisting of antisense nucleic acids. In one embodiment, the invention provides a method for decreasing extrajunctional expression of a protein encoded by a gene in a cell of a subject in need of decreasing extrajunctional expression of the protein, comprising contacting a cell of said subject with a nucleic acid comprising at least neuregulin-PTPase-Ras sensitive nAChR ε-subunit regulatory element (NRE), so that expression of a protein encoded by a gene in the genome operably linked to the NRE is decreased at extrajunctional sites. Further, the composition of this therapeutic antisense nucleic acid in a pharmaceutically acceptable carrier is provided. In another embodiment, a method for decreasing expression at a NMJ of one or more proteins encoded by a gene in a cell of a subject in need of decreased expression is provided, comprising contacting said cell with an antisense nucleic acid of a sequence which is complementary to the transcribed strand of the NRE, such that nucleic acid duplex, hybrid, or triplex is formed, and the contacted cell expresses a statistically significant decreased amount of the protein encoded by said gene or genes at the NMJ. Further, the composition of this nucleic acid in a pharmaceutically acceptable carrier, is provided. In these methods and compositions, an NRE complementary to the sequence shown in SEQ ID No. 3, or complementary to a 15 bp sequence that is greater than 70%, 80%, or 90% identical to the complement of the sequence shown in SEQ ID No. 3, is preferred. In other embodiments, the NRE sequence for antisense applications differs from the complement of SEQ ID No. 3 by four or fewer bases. In yet other embodiments, the sequence of the NRE for antisense applications is at least 70% identical to the complement of that of SEQ ID No. 3, is at least 80% identical to the complement of that of SEQ ID No. 3, or is at least 90% identical to the complement of that of SEQ ID No. 3.

In one embodiment, the methods and compositions of the antisense nucleic acids can be administered to the subject in vivo, for example, to a subject that has a tumor in a nerve tissue. In another embodiment, the antisense compositions can be transformed into a cell that is contacted ex vivo, for example, a cell previously taken from the subject and treated ex vivo, or a cell heterologous with respect to the subject.

The present invention features also methods for screening for drugs that can modulate expression of proteins at NMJ. In one embodiment, the invention provides method of screening a collection of chemical compounds comprising a library of suitable drug candidates, to identify a drug capable of modulating the response of the neuregulin-PTPase-Ras sensitive nAChR ε-subunit regulatory element. This method involves contacting a first set of cells carrying a regulatable reporter gene transcribed under the regulation of the NRE of the invention, with a compound selected from the library of suitable drug candidates, said contacting being in the presence of a neuregulin, and said cells capable of expressing a control reporter gene not similarly regulatable; and comparing expression of the reporter genes in said first set of cells to expression of the reporter genes in a second set of cells not contacted with said compound and under identical conditions otherwise, such that a statistically significant decrease in the expression of the regulated reporter gene from the first set of cells compared to the second set of cells, said unregulated reporter gene expression being used to control for transformation efficiencies in the sets of cells, indicates that the drug candidate suppresses the neuregulin response of the ε-subunit regulatory element.

In one embodiment of this method, the cells carry a reporter gene regulated by the NRE shown in SEQ ID No. 3, or a similar sequence containing no more than four alterations of sequence within the 15 bp. In yet other embodiments, the sequence of the NRE is at least 70%, identical to the complement of that of SEQ ID No. 3, is at least 80% identical to the complement of that of SEQ ID No. 3, or identical to the complement of that of SEQ ID No. 3. I a preferred embodiment of cells used as a component of the drug screens of the invention, the regulated reporter gene is selected from the group consisting of a luciferase, a β-galactosidase, a chloramphenicol transacetylase, and an alkaline phosphatase. In a particularly preferred embodiment, a method for screening for drugs that can modulate expression of proteins at the NMJ is provided, in which the cells to be contacted with a compound to be screened as a candidate drug harbor a construct in which the NRE operably linked to a reporter gene, is stably integrated into the genome of the cell, such that regulation of the reporter by the NRE, for example of SEQ ID No. 3, is filly retained. In yet other embodiments of this screen, the sequence of the NRE is at least 70% identical to the complement of that of SEQ ID No. 3, at least 80% identical to that of SEQ ID No. 3, or is at least 90% identical to the complement of that of SEQ ID No. 3. The stable integration of the NRE-reporter fusion obviates use of a second unregulated reporter gene construct in the cell. In these embodiments a preferred reporter gene is selected from the group consisting of a luciferase, a β-galactosidase, a chloramphenicol transacetylase, and an alkaline phosphatase.

In another embodiment of a screening method for drugs of the invention, each candidate in a collection of chemical compounds comprising a library of suitable drug candidates is contacted with a cell to identify a drug capable of modulating the expression within the cell of an NRE-linked reporter gene, featured in the present invention. This method comprises contacting a first set of cells carrying an NRE-regulated reporter gene with a test compound selected from the library of suitable drug candidates, said contacting being in the absence of a neuregulin. In one embodiment, the cells have the NRE-reporter gene construct stably integrated into the genome and retaining the NRE-regulation; in another embodiment, the cells are capable of expressing a control reporter gene not similarly regulated. Expression of the reporter gene in the first set of cells is compared to the expression of the reporter genes in a second set of cells not contacted with the drug candidate compound, the sets of cells being under identical conditions otherwise, such that the induction of a statistically significant increase in regulated reporter gene expression from the first set of cells compared to the second set of cells, said construct being stably integrated into cells or said unregulated reporter gene expression being used to control for the transformation efficiencies in each set of cells, indicates that the drug can substitute for the presence of neuregulin, or can supplement the level of the sum of endogenous and exogenous neuregulin by inducing expression of the NRE.

A further aspect provided is the chemical compound obtained by the method of these screens, in a pharmaceutically acceptable carrier, formulated for a preclinical trial in a test subject in need of such a drug.

The regulation of expression of genes by use of ε-subunit promoter nucleic acid sequences described herein can be used to treat, prevent, and/or reduce the severity of a number of neurological disorders and can thus be of therapeutic value. The term "neurological disorders" includes diseased or abnormal states in an individual which can include degenerative growth and development disorders, as well as degenerative diseases. Such neurological disorders can affect the central nervous system or the peripheral nervous system, or both. Also included are altered memory and decline in cognitive functions, as for example, resulting from normal aging processes. Neurological disorders which may be amenable to treatment with the compositions of the invention, including agonists or antagonists, can also include any disease where levels AChR of expression are altered.

In a preferred embodiment for therapy in cases of muscle or nerve tissue regeneration is the objective, the NRE is operatively linked to a gene encoding a neurotropic or neurotrophic factor, for example BDNF, CNTF, GNF, NTR-3, NTR4/5, NGF, GGF, and other factors identified that enhance nerve and muscle cell growth and proliferation. In another particularly preferred embodiment, the NRE is operatively linked to a gene encoding a protein that enhances formation of a neuromuscular synapse, for example, rapsyn, utrophin, dystroglycan, MuSK, laminin β–2, and agrin and similar components of synapses in nerve and muscle tissue.

An objective of the invention is to provide remediation of transynaptic expression deficiency (TSED), so that a patient suffering with a TSED condition in which insufficient amounts of a protein are expressed at a NMJ can be treated by the methods and compositions herein. TSED can be remediated by synapse-specific expression, which can be induced by administration of a neuregulin, of a gene under regulation of the NRE as provided in the present invention. TSED remediation is not limited to providing expression of one or more of the proteins listed herein; nor is remediation limited to providing the particular deficient protein. Rather, the methods and compositions of the invention can be used to induce junctional-specific expression of appropriate additional growth factors, structural proteins, alternative receptor subunits, and other proteins that contribute to development of a functional neuromuscular synapse.

Examples of neurological disorders which may be treatable with the compositions of the invention, include Alzheimer's disease, myasthenia gravis, and dementias associated with diseases such as Huntington's disease and Parkinson's disease.

Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies.

The methods and compositions of the invention can also be used in the treatment of autonomic disorders of the peripheral nervous system, which include disorders affecting the innervation of smooth muscle and endocrine tissue (such as glandular tissue). For instance, tachycardia is usually associated with an abnormally low level or activity of muscarinic AChRs in the striated muscle of the heart and can be treatable with the compositions of the invention. Likewise, atrial cardiac arrhythmias are also influenced by the activity of the muscarinic AChRs of the heart.

Also, nicotine itself is a cognitive enhancer. The compositions of the invention, by increasing the number of nicotinic receptors, may reduce or eliminate the "craving" for nicotine.

In the treatment of such diseases, it may be desirable to use the methods or administer the compositions of the invention in circumstances where an increase in the level of functional target at a synapse are desired. The compositions of the invention include an agent that up-regulates expression of a gene under control of the ε-promoter via modulations of transcription at a NRE recognition sequence such as SEQ ID No.:3, including an agent that is a nucleic acid, to be administered with a neuregulin such as heregulin or ARIA, a suitable homolog, or a peptide or a drug, capable of promoting at least one of the biological responses normally associated with such a sequence.

The present invention, by making available purified and recombinant nucleic acid constructs which are fusions of the ε-promoter NRE to suitable reporter genes, provides assays which can be used to screen for drugs which are either agonists or antagonists. By mutagenesis, and by structural surveys of the nucleic acid sequence as it exists in other organisms, additional screens are provided.

Heregulin, ARIA or other neuregulins can be used to supplement cell culture media for growth of postsynaptic target cells (e.g. muscle or nerve cells), and provide a means for inducing changes in expression and subcellular location of gene products. For instance, neuregulin, or an active fragment thereof, can cause an increase in synthesis of adult type AChRs, and can effect an accumulation of the receptors at the NMJ.

Motor cells having NMJs (NMJ) exhibit nAChRs as described herein, and contain similar subunits to neurons of the central and peripheral neural systems. Other neurotransmitter receptors of the central nervous system (CNS) for effectors other than acetylcholine, such as receptors for amino acids gamma-amino butyric acid (GABA), glycine, and glutamate, form ligand-gated ion channels having similar organizational and significant amino acid identity with the subunits of the nAChRs, and can be affected by members of the neuregulin class of protein effectors such as heregulin and ARIA. GABA and glycine receptors are concentrated beneath inhibitory boutons on central neurons, and glutamate receptors are concentrated at neurite contacts, presumably excitatory synapses.

Techniques for making fusion genes are well known. Essentially, the joining of various DNA fragments coding for different polypeptide sequences is performed in accordance with conventional techniques, employing blunt-ended or single-stranded nucleic acid termini for ligation, restriction enzyme digestion to provide appropriate termini, filling-in of cohesive ends as appropriate, alkaline phosphatase treatment to avoid undesirable joining, and enzymatic ligation. Alternatively, the fusion gene can be synthesized by conventional techniques including use of automated DNA synthesizers, for example, to provide a sequence comprising al 5 bp NRE regulatory element of the invention.

Moreover, variations of the nucleotide sequences and DNA molecules, both noncoding effectors and sequences that encode proteins, are also contemplated as being equivalent to those that are set forth in more detail, as will be appreciated by those or ordinary skill in the art. For example, it is reasonable to expect that in a protein such as neuregulin or ARIA, or a transcription factor such as rat Ets-2 provided herein, conservative alterations such as an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule, and can in fact provide a protein with more desirable properties.

Conservative replacements are those that take place within a family of amino acids that are related in the chemical properties of their side chains. Genetically encoded amino acids are can be divided into four families: (1) acidic amino acids are aspartate (D), and glutamate (E); (2) basic amino acids are lysine (K), arginine (R), and histidine (H); (3) nonpolar amino acids are alanine (A), valine (V), leucine (L), isoleucine (I), proline (P), phenylalanine (F), methionine (M), and tryptophan (W); and (4) uncharged polar amino acids are glycine (G), asparagine (N), glutamine (Q), cysteine (C), serine (S), threonine (T), and tyrosine (Y). The single letter designations for each of these amino acids, and as used in FIGS. 4 and 5 and SEQ ID No. 4, are given here in parentheses after each amino acid listed above. Phenylalanine, tryptophan, and tyrosine are sometimes classified as aromatic amino acids.

In similar fashion, the amino acids can be grouped as (1) acidic amino acids are aspartate and glutamate; (2) basic amino acids are lysine, arginine and histidine, (3) aliphatic amino acids are glycine, alanine, valine, leucine, isoleucine, serine, threonine, with serine and threonine optionally grouped as aliphatic-hydroxyl; (4) aromatic amino acids are phenylalanine, tyrosine and tryptophan; (5) amide amino acids are asparagine and glutamine; and (6) sulfur-containing amino acids are cysteine and methionine. (see, for example, *Biochemistry*, 2nd ed, Ed. by L. Stryer, W. H. Freeman and Co.:1981). Whether a change in the amino acid sequence of a peptide results in a functional protein homolog can be readily determined by assessing the ability of the variant peptide to effect an appropriate response in cells in a fashion similar to the wild-type protein. Peptides in which more than one replacement has taken place can readily be tested in the same manner. For example, proteins that bind specific DNA sequences may be engineered (Ladner, R. C. et al., U.S. Pat. No. 5,096,815), to obtain mutants with increased or decreased affinity. Further, mutagenesis of a peptide linked to a filamentous phage enables selection of variants with a desired property, for example, variants of rat Ets-2 with altered affinity for the NRE of SEQ ID No. 3, or with altered affinity for an NRE that varies by one to four nucleotides from that SEQ ID No. 3. Proteins that bind a variety of other targets, especially protein targets (Ladner, R. C. et al., U.S. Pat. Nos. 5,233,409 and 5,403,484) may be engineered and used in the present invention to obtain, for example, a rat Ets-2 derivative with increased affinity for the appropriate RNA polymerase of a heterologous host cell.

The 45 kD protein heregulin-a (HRG-a), cloned from an mRNA-derived MDA-MB231 cell library, and several complementary DNA clones encoding related HRGs are members of the epidermal growth factor (EGF) family (Holmes et al. 1992 *Nature* 256:1205, incorporated by reference herein). A 44 kD glycoprotein secreted by transformed rat fibroblasts, termed Neu differentiation factor (NDF), has been cloned and expressed (Wen et al. 1992 *Cell* 69:559, incorporated by reference herein). These, several additional factors, and ARIA are transcribed from the same gene (Moscoso et al., Dev. Biol. 172:158–169, 1995), using alternative splicing. These and other neurotrophic factors, termed neuregulins, to exist in vivo as glycoproteins, and have molecular weights in the range of 40 kd to 45 kd. They possess an immunoglobulin-like domain as well as an EGF-like domain. ARIA also contains two stretches of amino acid residues in the amino terminal extracellular domain, referred to herein as Nex-1 and Nex-2, which can be divergent in sequence from the corresponding amino acid positions in rat NDF, the human heregulins, and the glial growth factors.

DEFINITIONS

The present invention relates to a nucleic acid comprising a "neuregulin response element" (NRE) and its therapeutic applications and uses in methods for drug screening. Transcription modulated by the presence upstream of an NRE sequence directs gene product expression to a neuromuscular synapse, and represses gene product expression at extrajunctional sites.

As herein defined, an NRE is a DNA sequence regulatory element which mediates at least one of the following functions: responsiveness to neuregulin, responsiveness to activated Ras, and responsiveness to a dual specificity PTPase. In a preferred embodiment, an NRE comprises nucleotides located at −55 to −69 from the transcription start site of the gene for the $\epsilon$-subunit of nAChR in the rat (SEQ ID No. 3), and is the site for transcriptional responsiveness of this gene to neuregulin, activated Ras, and dual specificity PTPase. The invention features also NRE sequences that are homologs of the rat nAChR $\epsilon$-subunit, for example NRE sequences observed in the genome of other mammals such as human and mouse. The invention includes also NRE sequences that differ from the sequence shown in SEQ ID No. 3 by mutation, including and not limited to mutation by substitution, deletion, addition, said substitutions including both transitions and transversions, if the change or changes do not cause a defect in NRE function with respect to response to one or more of the agents included here in the definition. If for example an NRE nucleotide sequence differs from the rat $\epsilon$-subunit NRE of SEQ ID No. 3, it is preferable that the difference is at four or fewer nucleotides. As shown herein, alterations to the NRE can be achieved by site-directed mutagenesis primers which have been chemically synthesized, and the NRE itself may be synthesized de novo, or may be isolated from a mammalian promoter.

The terms "protein", "polypeptide" and "peptide" are used interchangeably herein.

By "purified" is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type (but water, buffers, and other small molecules, especially molecules having a molecular weight of less than 5000, can be present). The term "pure" as used herein preferably has the same numerical limits as "purified" immediately above.

The term "isolated" as used herein refers to a peptide, DNA, or RNA molecule separated from other peptides, DNAs, or RNAs, respectively, that are present in the natural source of the macromolecule.

As used herein, the term "nucleic acid molecule" is intended to include DNA molecules (e.g., cDNA or genomic DNA), RNA molecules (e.g., mRNA), and analogs of DNA, such as peptide nucleic acid molecules (PNA), phosphorothioate DNA, and DNA based on a peptide analog backbone such as a trans-olefin peptidomimetics and phosphonate peptidomimetics. Peptide nucleic acid (PNA) is an oligomer in which the charged phosphate-ribose backbone has been eliminated and replaced with an uncharged polyamide backbone (Egholm M., et al. *J Am. Chem. Soc.,* 114:1895–1897; 1992). These oligomers have been reported to resist nuclease and protease degradation (Egholm M., et al. *Nature,* 365:566–568; 1993.). Furthermore, the binding affinities of PNA for its complementary single-stranded PNA has been shown to exceed that of comparable DNAs (Egholm M., et al. *J. Am. Chem. Soc.,* 114:1895–1897; 1992).

As used herein, a "naturally-occurring" nucleic acid molecule refers to an RNA or DNA molecule having a nucleotide sequence and structure of backbone that occurs in nature, whether it is prepared by isolation from an organism or is chemically synthesized. A nucleic acid can be chemically synthesized using a commercially available automated synthesizer and reagents, or custom made by a commercial supplier (for example, PerSeptive Biosystems, Framingham, Mass.). A "chimeric nucleic acid" is a covalently linked first base sequence with a second base sequence of different chemical character, for example, a PNA strand covalently linked to a DNA or RNA strand.

As used herein, the term "derived from" with respect to a nucleic acid sequence, indicates that the sequence is selected from a known naturally-occurring sequence, or is a homolog of that sequence, or a naturally-occurring polymorphic variant, or a natural or induced mutation of that sequence. The sequence can be isolated from the genome of an organism, or may be produced from a vector by restriction digestion and further purification, or it may be synthesized chemically, each of these performed by techniques known to one of ordinary skill in the art and described in art referenced herein and incorporated by reference.

The term "isolated" nucleic acid, as used herein, means a nuclic acid of nucleotide sequence that is free of sequences which naturally flank the nucleic acid (i.e., sequences located at the 5' and 3' ends of the nucleic acid) found in the genomic DNA of the organism from which the nucleic acid is derived. As used herein for the embodiment of an isolated NRE, an isolated nucleic acid molecule encoding an NRE can retain less than 10 bp, less than 15 bp, less than 20 bp, less than 25 bp, or less than 30 bp of 5' flanking nucleotide sequence, and can retain less than 15 bp, less than 30 bp, less than 45 bp, or less than 60 bp of 3' flanking nucleotide sequence which naturally flank the nucleic acid molecule in genomic DNA of the cell from which the nucleic acid is derived (e.g. a rat muscle cell). Moreover, an "isolated" nucleic acid molecule, such as an RNA molecule, can be free of other cellular material.

A "portion" of a nucleic acid sequence refers to a subsequence of a nucleic acid sequence. The "portion" can be an entire nucleic acid sequence or any subsequence thereof. In preferred embodiments, a portion is at least about 6 nucleotide bases in length, more preferably at least about 12 bases in length, still more preferably at least about 15 bases in length.

The term "can be degraded in vivo", as used herein, refers to a polymer that includes a bond that can be cleaved in vivo, either enzymatically or non-enzymatically. For example, natural nucleic acids can be cleaved by nucleases that attack the sugar-phosphate backbone, at any phosphodiester bond or at specific sites of defined base sequence.

In addition to nucleic acid molecules with sequences of interest, the invention contemplates use of nucleic acid molecules which are antisense thereto. An "antisense" nucleic acid comprises a nucleotide sequence which is complementary to a "sense" nucleic acid, e.g., complementary to the mRNA-identical strand of a double-stranded DNA molecule or complementary to an mRNA sequence with T of DNA equivalent to U of RNA. Antisense constructs of the present invention, by antagonizing the normal biological activity of promoter-specific DNA, can be used in the therapeutic context, to inhibit or decrease expression of nerve or muscle-specific genetic information that is synthesized under regulation of the NRE of the invention.

The terms "homology" or "homologous" or "homolog" as used with respect to nucleotide or amino acid sequences herein refer to an extent of sequence identity relationship between two polypeptide molecules or between two nucleic acid polymer molecules. When a position in both of the two compared sequences is occupied by the same base or amino acid monomer, e.g., if a position in each of two DNA molecules is occupied by an adenine, then the molecules are identical at that position. The homology between two sequences is a function of the number of matching or identical subunits monomers shared by the two sequences. For example, if 6 of 10 positions in two sequences are identical, then the two sequences are 60% homologous. Sequence homology can be optimized by aligning the two sequences for example by inserting one or more spaces into one of the sequences. By way of example, ATTGCC and TATGCC are 50% identical, and TATCCGCC and TATGCC share greater than 50% homology if the latter sequence is aligned TAT—GCC .

As used herein, the term "heterologous cell" or "heterologous gene" includes a cell or gene that does not occur naturally as part of a tissue, organ, or the genome in which it is present or which is found in a location or locations in the genome that differs from that in which it occurs in nature. A heterologous cell is not endogenous to the subject into which it is introduced, but has been obtained from another subject, which subject can be conspecific or congeneric.

"Heterologous DNA" is not endogenous to the cell into which it is introduced, but has been supplied exogenously using genetic techniques known to one of ordinary skill in the art. Generally, although not necessarily, such DNA encodes RNA and proteins that are not normally produced by the cell in which it is expressed, or are produced in a genomic context different from that of the vector bearing the heterologous DNA supplied exogenously to the cell. Heterologous DNA can also be referred to as foreign DNA. Any DNA that one of ordinary skill in the art would recognize or consider as heterologous or foreign to the cell in which is expressed is herein encompassed by heterologous DNA.

The term "coding region" refers to the region of the DNA sequence comprising codons which are translated into amino acid residues. In another embodiment, the antisense nucleic acid molecule is antisense to a "noncoding region" of the coding strand of a nucleotide sequence of interest. The term "noncoding region" refers to 5' and 3' sequences which flank a coding region and are not translated into amino acids (i.e., also referred to as 5' and 3' untranslated regions).

The term "regulatory element" refers to a nucleic acid comprising a nucleotide sequence which is capable of controlling the expression of a gene to which it is operably linked. The term regulatory element is intended to include a nucleotide sequence which, alone or together with one or more other nucleotide sequences, is capable of controlling expression of a gene to which the regulatory sequence is operably linked. The term "promoter" as used herein refers to the promoter region, the 5' flanking sequence upstream from initiation of transcription and intended to include for example, the TATA box for RNA polymerase complexation with the template, 5' enhancers, and recognition sequences for regulatory proteins. The promoter region as used herein can be 100 bp, 500 bp, 2,000 bp or 5,000 bp of DNA, located upstream for example of the nAChr ε-subunit gene. By "regulatory element" is meant the smaller, functionally specific sequences within for example, a termination region or a promoter region, such as but not limited to, the TATA box, the consensus sequence specifying binding of the Ets family of proteins, and the consensus sequence specifying binding of the serum response protein, along with polyadenylation signals and other DNA elements regulating expression of a gene. Such regulatory sequences are known to those skilled in the art and are described in Goeddel, *Gene Expression Technology: Methods in Enzymology* 185, Academic Press, San Diego, Calif. (1990). A promoter region typically contains several regulatory elements.

The term "5' flanking sequence" is intended to include a nucleotide sequence located 5', i.e., upstream, of the transcription initiation site or other point of reference, of a gene. Such 5' flanking sequences encompass one or more promoter domains as defined herein. In one embodiment, the 5' flanking sequence is the rat mAchR ε-subunit 5' flanking sequence having a regulatory sequence at −55 to −69 to the transcriptional start site.

The term "3' flanking sequence" is intended to include a nucleotide sequence located 3', i.e., downstream of the polyadenylation signal of a gene.

"Operably linked" is intended to mean that the nucleotide sequence of the foreign or heterologous gene of interest, exogenously supplied by the skilled artisan, is linked to the regulatory element in a manner which allows expression of that gene in a host cell (or in a cell extract) with the expected characteristics of the regulatory element. The term operably linked is intended to include a linkage that allows the regulatory element to control the expression of the gene. In a preferred embodiment, a regulatory element is chemically linked to the heterologous gene, such as by natural phosphodiester linkage between two nucleotides. The regulatory element can be linked directly to the gene of interest. Alternatively, the regulatory element can be linked indirectly to the gene of interest, such as by a linker, e.g., a nucleotide sequence. Such a linker can vary in length and may contain nucleotide sequences that are recognized by restriction enzymes.

As used herein, the terms "modulated" or "modulation" refer to the ability of an agent to alter the amount of transcription of a gene in response to an alteration of a quantity of an agent. An agent can modulate gene expression positively or negatively. The agent can be supplied exogenously, for example, exogenously supplied neuregulin that is added to the culture medium and that acts at a receptor on a cell to cause a series of biochemical alteration in the MAP kinase signaling pathway within a cell. Other agents can act endogenously, for example, transformation of a cell with a vector that causes of an alteration in the genotype, for example by providing multiple copies of a gene for a dual specificity PTPase or for an activated Ras gene, can perturb the signaling pathway to modulate expression of a gene either by increasing or decreasing gene expression.

As used herein, the term "dual specificity PTPase" refers to the prototype and also to subsequently discovered those protein phosphatases that remove phosphates from both classes of substrates, phosphorylated tyrosines, and phosphorylated threonines and serines. The term "dual" indicates that a class of the family protein phosphatases, originally described as specific either for tyrosine or for serine and threonine, in fact can remove phosphate groups from both classes of substrate.

"Activated Ras protein" or "Ras+" as used herein means the product of a mutant Ras gene which is active in the MAP kinase signaling pathway without further alteration. In certain embodiments, it is supplied to cells exogenously in the form of a construct bearing the gene for this protein, as a test for NRE function.

The term "muscle cell" as used herein, refers to muscle precursor cells or myoblasts, to primary myotube cultures, and to stable cell lines such as rat L6 and L6E9, and mouse C2, C2C12, MM14, and $BC_3H1$ cell lines.

The term "nerve cell", as used herein, refers to pre-mitotic nerve precursors and differentiated postmitotic cells of the central and peripheral nervous system. The differentiated nerve cells are characterized by having an axon cell body and dendrites, and are capable of transmitting and receiving an electrical signal. Pre-mitotic immortalized nerve cell lines are available, and primary nerve cells can be cultured, and include line NG108.

The term "culture medium" is recognized in the art, and refers generally to any substance or preparation used for the cultivation of living cells. Accordingly, a "tissue culture" refers to the maintenance or growth of tissue, e.g., explants of organ primordia or of an adult organ in vitro so as to preserve its architecture and function. A "cell culture" refers to a growth of cells in vitro; although the cells proliferate they do not organize into tissue per se.

As used herein, the terms "vector", "plasmid" or "construct", used interchangeably, refer to a nucleic acid molecule capable of transporting another nucleic acid to which it has been linked. The term "expression vector" includes plasmids, cosmids, phages, or virus-based DNA molecules capable of synthesizing the subject protein encoded by the respective recombinant gene carried by the vector, plasmid, or construct, when transformed into a suitable host cell. In general, preferred vectors are those capable of autonomous replication and/expression of nucleic acids to which they are linked, except however if the objective of the transformation of DNA is to produce a stably maintained transformant cell in which the foreign DNA becomes integrated into the genome. Moreover, the invention is intended to include such other forms of vectors which serve equivalent functions and which become known in the art subsequently hereto.

As used herein, the terms "transfection" or "transformation", used interchangeably, mean the introduction of an exogeous nucleic acid, e.g., an expression vector, into a recipient cell by nucleic acid-mediated gene transfer. In general, the exogenous nucleic acid or a portion thereof is comprised of foreign or heterologous DNA.

By "gene product" it is meant a molecule that is produced as a result of transcription of a gene. Gene products include RNA molecules transcribed from a gene, as well as proteins translated from such transcripts.

A suitable host for the invention can be a subject or a patient. The term "subject," as used herein, refers to a living animal or human in need of therapy for, or susceptible to, a condition, for example transynaptic expression deficiency, which is remediable through treatment with the nucleic acids, proteins, or drugs of the invention. In preferred embodiments, the subject is a mammal, including humans and non-human mammals such as higher apes, dogs, cats, pigs, cows, sheep, goats, horses, rats, and mice. In the most preferred embodiment, the subject is a human. The term "subject" does not preclude individuals that are normal in all respects. The subject can formerly have been treated surgically or by chemotherapy, and can be under treatment, and can have been so treated in the past.

The term "patient," as used herein, refers to a human subject who has presented at a clinical setting with a particular symptom or symptoms suggesting treatment by the compositions or methods of the invention. A patient's diagnosis can alter during the course of disease progression, such as development of further disease symptoms, or remission of the disease, either spontaneously or during the course of a therapeutic regimen or treatment.

As used herein, the term "animal" refers to mammals, preferably mammals such as humans. As used herein, a "transgenic animal" is any animal, preferably a non-human mammal, bird, amphibian, fish, fly, or worm, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a protein that would not naturally be expressed in the absence of the genetic manipulation. Further, "transgenic animal" or "transgenic cell" or "recombinant cell" also includes those animals or cells in which gene expression of one or more genes is caused by human intervention, including both recombinant and antisense techniques. A transgenic animal includes an animal which by virtue of genetic engineering, such as disruption of a gene by insertion of foreign DNA, has lost function of a gene, e.g., a rat "knocked out" for the gene encoding Ets-2.

The present invention provides, in one aspect, methods for expression of genes in nerve or muscle cells that are genetically modified to express the gene at a neuromuscular junction or to modulate expression of the gene at an NMJ relative to extrajunctional expression. From the description provided herein, the skilled artisan will appreciate the embodiments of the subject cells that can be practiced, including those which are generated by the use of gene constructs in addition to those provided in the examples herein.

Vectors for Cell Transformation

It will be understood that a wide range of vectors, such as described below, can be used for recombinantly expressing NRE-linked genes in target nerve or muscle cells. Such vectors can be constructed using methods well known in the art, including, without limitation, the standard techniques of restriction endonuclease digestion, ligation, plasmid and DNA and RNA purification, DNA sequencing, and the like as described, for example in Sambrook, Fritsch, and Maniatis, eds., *Molecular Cloning: A Laboratory Manual.,* (Cold Spring Harbor Laboratory Press, Cold Spring Harbor, N.Y. 1989). Most practitioners are familiar with the standard resource materials as well as specific conditions and procedures. However, for convenience, the following paragraphs may serve as a guideline.

To generate an appropriate gene construct, nucleic acid corresponding to the intended gene may be obtained from mRNA or genomic DNA present in any of a number of eukaryotic cells in accordance with protocols described herein, as well as those generally known in the art. To illustrate, cDNA encoding a protein can be obtained by isolating total mRNA from a cell expressing that protein, e.g., a muscle or a neural tissue. Double stranded cDNAs can then be prepared from the total mRNA, and subsequently inserted into a suitable plasmid or bacteriophage vector using any one of a number of known techniques. A gene encoding a protein can also be cloned using established polymerase chain reaction techniques in accordance with the nucleotide sequence information provided by the invention.

Any of the methods known to the art for the insertion of DNA fragments into a vector may be used to generate expression constructs of the present invention. See, for example, Sambrook et al., herein; and Ausubel et al. eds. *Current Protocols in Molecular Biology,* (John Wiley & Sons, New York 1992). These methods may include in vitro DNA recombinant and synthetic techniques and in vivo genetic recombination.

A heterologous gene will typically be operably linked to a nAchR $\epsilon$-subunit promoter transcriptional regulatory NRE sequence of the present invention to regulate expression of the gene in a particular manner. In certain embodiments, this transcriptional regulatory sequence can be highly regulated with respect to activity, both temporally and spatially. Thus, the promoter of the invention can be is most useful in particular tissues or cell types. Where the $\epsilon$-subunit promoter can be obtained from a non-human mammal, the mammal may be homologous (the same species as the mammal to be transfected) or non-homologous (a different species), and the function will be similar or identical. The identity within a 15 bp sequence can be 90% (1 bp different), 85% identical (2 bp different), 80% identical (3 bp different), or 70% identical (4 bp different), and maintain substantially equivalent regulation with respect to regulation by a neuregulin, and by PTPase and activated Ras or equivalent proteins within the same signal transduction pathway . Equivalence of function can be determined without undue experimentation by the methods provided herein.

The promoter can be introduced into vectors using standard methods in the art (see e.g., Sambrook et al. and Ausubel et al. cited herein).

In addition to nAchR $\epsilon$-subunit gene promoter transcriptional regulatory sequence, the vectors useful for preparing the recombinant genes of this invention typically contain one or more other elements useful for optimizing expression in the host animal. To illustrate, the gene construct may contain a non-regulated promoter such as the MEK promoter (Huggenvik, J. I. (1991) Molec. Endocrinol. 5:921–930) described in the Examples, or the thymidine kinase TK promoter (available from ProMega, Madison, Wis.). Further, the gene construct may include transcription termination elements, such as to direct polyadenylation of an mRNA transcript, as well as intronic sequences. For example the coding sequence of the recombinant gene can be flanked at its 3' end by SV40 sequences (SV40intron/pA) which add the transcription termination and polyadenylation signals to the transcript. In yet other embodiments, the regulated gene can include appropriate intron sequence(s) interrupting the coding sequence. In many instances, transcription of a recombinant gene in mammals is increased by the presence of one or more introns in the coding sequence.

In still other embodiments, the gene construct can include additional elements which facilitate its manipulation in cells (e.g., bacterial) prior to transformation into the intended recipient eukaryotic cell. For instance, the vector may include origin of replication elements for amplification in prokaryotic cells, and can include an origin of replication suitable to the eukaryotic target cell. For construction of a stably integrated element in a target cell for therapy or for a cell to be used in a drug screen, an origin of replication is not preferred. Moreover, the gene construct can include selectable markers for isolating recipient cells that have been successfully transformed, for example, bacterial cells used for amplifying the construct. Selectable marker genes can encode proteins necessary for the survival and/or growth of transfected cells under selective culture conditions. Typical selection marker genes encode proteins that, for example: (i) confer resistance to antibiotics or other toxins, e.g., ampicillin, tetracycline or kanamycin for prokaryotic host cells, and neomycin, hygromycin or methotrexate for mammalian cells; or (ii) complement auxotrophic (nutritional) deficiencies of the cell, for example, a requirement for exogenously added histidine or tryprophan.

The vectors carrying the gene constructs may be administered in any biologically effective carrier, e.g. any formulation or composition capable of effectively transfecting cells ex vivo or in vivo with the expression construct. Efficient DNA transfer methods have been developed for myoblast and myotube cells and are cited in references in the Examples herein. Approaches include insertion of the described gene construct in viral vectors including recombinant retroviruses, adenovirus and adeno-associated virus, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramicidin S, artificial viral envelopes or other such intracellular carriers, as well as direct injection of the gene construct, or calcium phosphate co-precipitation. It will be appreciated that because transformation of appropriate target cells represents the critical first step in gene therapy, choice of the particular gene delivery system will depend on such factors as the phenotype, e.g., the degree of differentiation the cell has undergone, if any. Another factor in the selection of the appropriate transformation formulation is the consideration raised by ex vivo transformation versus in vivo transfection, with the latter requiring consideration of the route of administration, e.g. locally or systemically.

A preferred approach for both ex vivo or in vivo introduction of the subject gene constructs into a cell is by use of a viral-based DNA vector containing the gene construct. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors are generally understood to be one of the recombinant gene delivery system of choice for the transfer of exogenous genes into cells, particularly into humans cells. (see e.g., Hawley R. G., et al (1994) *Gene Therapy* 1:136–38)). These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses as a gene delivery system, and defective retroviruses are well characterized for use in gene transfer for gene therapy purposes. Thus, recombinant retrovirus can be constructed in which part of the retroviral coding sequence (gag, pol, env) has been replaced by the gene to be delivered, rendering the retrovirus replication defective. The replication defective retrovirus is then packaged into virions which can be used to infect a target cell through the use of a helper virus by standard techniques. Protocols for producing recombinant retroviruses and for infecting cells ex vivo or in vivo with such viruses can be found in Ausubel et al., herein, Sections 9.10–9.14 and other standard laboratory manuals. Examples of suitable retroviruses include pLJ, pZIP, pWE and pEM which are well known to those skilled in the art. Examples of suitable packaging virus lines for preparing both ectropic and amphotropic retroviral systems include ΨCrip, ΨCre, Ψ2 and ΨAm.

Retroviruses have been used to introduce a variety of genes into many different cell types, by both ex vivo and in vivo protocols (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. Nos. 4,868,116; 4,980,286; PCT Application WO 89/07136; PCT Application WO 89/02468; PCT Application WO 89/05345; and PCT Application WO 92/07573).

Exemplary retroviral vectors have been described that yield a high titer virus capable of efficiently transfecting and expressing genes in undifferentiated embryonic cells (Hawley et al (1994) *Gene Therapy* 1:136–38). These vectors contain a selectable marker under the transcriptional control of an internal murine pgk promoter and unique restriction sites for insertion of genes downstream of a variant LTR from the retroviral mutant PCMV (PCC4 embryonal carcinoma cell-passaged myeloproliferative sarcoma virus).

The art demonstrates that it is possible to limit the infective spectrum of retroviruses, and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for stem cell surface antigens to the viral env protein (Roux et al. (1989) *PNAS* 86:9079–9083; Julan et al. (1992) *J. Gen. Virol.* 73:3251–3255; and Goud et al. (1983) *Virology* 163:251–254); or coupling cell surface ligands to the viral env proteins (Neda et al. (1991) *J. Biol. Chem.* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins).

In addition to viral transfer methods, such as those illustrated above, non-viral methods can also be employed to cause expression of a heterologous gene in the cells of nerve or muscle origin. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the hematopoietic gene construct by the targeted cell. Exemplary gene delivery systems of this type include liposomal derived systems, poly-lysine conjugates, and artificial viral envelopes.

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). It will also be appreciated that effective delivery of the subject nucleic acid constructs via receptor-mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al. (1993) *Science* 260–926; Wagner et al. (1992) *PNAS* 89:7934; and Christiano et al. (1993) PNAS 90:2122). Transfection in muscle cells using calcium phosphate precipation has been described by Sapru, M. K., et al., 1994, J. Biol. Chem. 269:27811–27814, and by Chahine, K. G., et al., (1992) Devel. (Cambr.) 115:213–219. In another embodiment of the invention the nucleic acid is introduced into muscle cells by particle bombardment, as described in Yang, N.-S. and Sun, W. H. (1995) *Nature Medicine* 1, 481.

Nucleic Acids

The invention further contemplates the use of nucleic acids, polynucleotides, and oligonucleotides that are alternatives to, or analogs of, naturally occurring deoxynucleic acid with its sugar-phosphate backbone, or synthetic oligo- and polynucleotide sugar-phosphate polymers. While native single-stranded phosphodiester DNA has been considered for in vitro or in vivo applications these unmodified oligonucleotides are highly susceptible to degradation by nucleases (Wickstrom E. *J. Biochem. Biophys. Methods.* 13:97–102, 1986; Cazenave C., Chevrier et al. *Nucleic Acids Res.* 15:10507–10521, 1987; Ceruzzi M. and Draper K. *Nucleosides Nucleotides* 8:815–818, 1989) and, as such may be inappropriate as antisense therapeutics for certain therapeutic applications. Methods have been developed to chemically modify the phosphodiester DNA to improve its stability (Goodchild *J. Bioconj. Chem.* 1:165–187, 1990). Among the many possible modified DNAs, phosphorothioates, in which a nonbonding oxygen in the phosphate backbone is replaced with a sulfur (Iversen P. In *Antisense research and applications,* Crooke ST, Lebleu B. eds. CRC Press, Ann Arbor Mich., 1993 p 462–469), have found considerable application. The native phosphodiester DNA and RNA, and phosphorothioate nucleic acids are included in the present invention, as their properties may be superior for some applications. Phosphorothioates may be further modified to alter charge, and kinetics of administration can be varied to render delivery less harmful to the subject recipient.

A nucleic acid molecule may be single-stranded or double-stranded, but preferably is single-stranded. In preferred embodiments, the nucleic acid is DNA, PNA, phosphorothioate DNA, or RNA.

In a preferred embodiment, an isolated nucleic acid molecule of the invention comprises a base nucleotide sequence with a specific linear order of the bases adenine, guanine, cystosine, thymine or uracil, or modified derivatives of these bases (e.g., methyladenine, and hydroxymethyluracil). A nucleic acid can contain non-naturally occurring bases, such as 5-fluorouracil, or "unusual" bases, such as ribothymidine or others, e.g., such as are found in tRNA. Other modified bases are known to those with skill in the art. The term "unusual base," is known in the art, and refers to uncommon bases such as pseudouracil or ribothymine, found, e.g., in tRNA. It is also possible to modify the structure of the oligonucleotides and polynucleotides for such purposes as enhancing therapeutic or prophylactic efficacy, or stability (e.g., ex vivo shelf life and resistance to nucleolytic degradation in vivo).

A nucleic acid molecule having a known nucleotide sequence can be isolated using standard molecular biology techniques (e.g., as described in Sambrook, J., Fritsh, E. F., and Maniatis, T. (1989) *Molecular Cloning: A Laboratory Manual.* 2nd, ed., Cold Spring Harbor Laboratory, Cold Spring Harbor, N.Y.). For example, mRNA can be isolated from cells (e.g., by the guanidinium-thiocyanate extraction procedure of Chirgwin et al. (1979) *Biochemistry* 18:5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon knowledge of the nucleotide sequence or fragments of the sequence, as will be appreciated by those with skill in the art, and are used to obtain and clone an isolated nucleic acid adjacent to the primer.

In certain embodiments, an isolated nucleic acid molecule useful in the compositions and methods of the invention is at least about 12 nucleotides in length and hybridizes under stringent conditions to a nucleic acid molecule comprising the nucleotide sequence of interest. In other embodiments, a nucleic acid is at least 15, 20, 30, 50, or 100 nucleotides in length. As used herein, the term "hybridizes under stringent conditions" is intended to describe conditions for annealing to form a double-stranded molecule(hybridization), and washing, under which conditions nucleotide sequences at least 60% homologous to each other typically remain hybridized to each other. Preferably, the conditions are such that sequences at least 65%, more preferably at least 70%, and even more preferably at least 75% homologous to each other typically remain hybridized to each other. Such stringent conditions are known to those skilled in the art and can be found, e.g., in *Current Protocols in Molecular Biology,* Ausubel, F. et al., John Wiley & Sons, N.Y. (1989), 6.3.1–6.3.6. A preferred, non-limiting example of stringent hybridization conditions is hybridization in 6X sodium chloride/sodium citrate (SSC) at about 45° C., followed by one or more washes in 0.2× SSC, 0.1% SDS at 50–65° C. Preferably, an isolated nucleic acid molecule of the invention that hybridizes under stringent conditions to a sequence of the invention corresponds to a naturally-occurring nucleic acid molecule.

The skilled artisan will appreciate that antisense nucleic acids can be designed according to methods known in the art, e.g., according to the rules of Watson and Crick base pairing. The antisense nucleic acid can be complementary to an entire message strand, or to only a portion thereof. In one embodiment, an antisense nucleic acid molecule is antisense to a "coding region" of the coding strand of a nucleotide sequence. Antisense nucleic acid may be complementary to either or both of a coding region and an adjacent noncoding region. An antisense molecule can form a duplex with its DNA complement, or a hybrid with mRNA to which it is complementary. In some embodiments, an antisense can form a triplex structure with double-stranded DNA.

The antisense nucleic acid molecule may be complementary to an entire coding region, but more preferably is an oligonucleotide which is antisense to only a portion of a coding or noncoding region. For example, an antisense oligonucleotide may be complementary to the region surrounding the transcription start site of a gene, such as the NRE of the present invention and its flanking sequences. An antisense oligonucleotide can be, for example, about 15, 20, 25, 30, 35, 40, 45 or 50 nucleotides in length. An antisense nucleic acid of the invention can be constructed using chemical synthesis and/or enzymatic reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., peptide nucleic acid or chemically modified phosphorothioate nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid).

Promoters and Regulatory Elements

In a preferred embodiment, the regulatory element of the invention is the 15-base pair (bp) sequence upstream of the start site of transcription of the ε-subunit of nAChR, in the rat at nucleotides −55 to −69, depicted as SEQ ID No. 3. This sequence in the present invention is shown to be regulated in response to the presence of a neuregulin, activated Ras, and PTPase. In a preferred embodiment, the regulatory element of the invention is the 15 base pair (bp) sequence upstream of the start sit of transcription of the ε-subunit of nAChr, in the rat a nucleotide −55 to −69, depicted as SEQ ID No. 3. This sequence is sufficient and necessary for transcription to be regulated by neuregulins, activated Ras, and PTPase.

A regulatory element can include a portion of a promoter to which an RNA polymerase binds and which usually contains a TATA box. Such a regulatory element is responsible for the basal transcription of a gene. A regulatory element can be a portion of a promoter to which a protein, such as a transcription factor, binds and modulates extent of transcriptions initiation. A promoter lacking a TATA box often contains another consensus sequence for recognition of a positive regulatory transcription factor, such as an E-box for recognition of an Ets protein.

A regulatory element can be an enhancer or portion thereof. Generally, an enhancer is an element which modifies the basal transcription of a gene which it controls. An enhancer element can be located several kilobases away from the gene whose expression it affects and it can be located in any part of a gene, such as in 3' or 5' noncoding sequences and in introns. Regulatory elements also include silencers, i.e., DNA elements which will reduce the level of transcription of a gene.

Preferred regulatory elements within the scope of the invention include tissue-specific regulatory elements. The term "developmental- or differentiation-specific regulatory element" is intended to include a regulatory element that controls expression of an foreign gene to which it is operably linked in a specific cell type, cell location, or at a specific time. A tissue as defined herein can be a cell site, for example a NMJ or synapse in a muscle cell. Tissue- or cell-specific expression of a gene occurs predominantly in the cell or tissue in which the regulatory element is active, such as a differentiated cell (and not in an undifferentiated or precursor cell), for example, a gene like that of ε-subunit of nAChR, that is expressed in an adult muscle cell but not in an embryonic cell can be said to be developmentally specific to adult muscle cells.

Regulatory elements of the invention can be inducible. The term inducible regulatory element is intended to mean that the expression of a gene that is controlled at least in part by a regulatory sequence can be modified by, for example, exposing the cell to a specific compound or to a specific condition. Inducers within the scope of the invention include agents which interact with a receptor on the surface of a cell or within a cell and include among others differentiation factors, growth factors, hormones, cytokines, neuregulins, or chemicals. Regulatory elements which are inducible are well known in the art. In one embodiment, the regulatory element is inducible and cell-specific, for example, induction of expression of genes for nAChR subunits by the protein heregulin or ARIA. Regulatory elements can also be induced by a change in the environment of the cell or tissue, such as a change in temperature, (e.g., an increase in temperature) and include, for example, nucleotide sequences termed "heat shock elements". Further, a regulatory element can be induced by exposure to light of a certain wavelength, such as ultraviolet light. Inducible regulatory systems for use in mammalian cells are known in the art, for example systems in which gene expression is regulated by heavy metal ions (Mayo et al. (1982) *Cell* 29:99–108; Brinster et al. (1982), *Nature* 296:39–42; Searle et al. (1985) *Mol. Cell. Biol.* 5:1480–1489), heat shock (Nouer et al. (1991) in *Heat Shock Response*, e.d. Nouer, L., CRC, Boca Raton, Fla., pp 167–220; Morris T. (1991) *Mol. Cell. Biology* 11:544), hormones (Lee et al. (1981). *Nature* 294:228–232; Hynes et al. (1981) *Proc. Natl. Acad. Sci.* USA 78:2038–2042; Klock et al. (1987) *Nature* 329:734–736; Israel & Kaufman (1989) *Nucl. Acids Res.* 17:2589–2604 and PCT Publication No. WO 93/23431), tetracycline (Gossen, M. and Bujard, H. (1992) *Proc. Natl. Acad. Sci.* USA 89:5547–5551 and PCT Publication No. WO 94/29442) or FK506 related molecules (PCT Publication No. WO 94/18317)

Other preferred ε-subunit regulatory elements include such fragments of 5' flanking sequence of an ε-subunit gene of length such as 2.0 kB, 1.5 kB, 1.0 kB, or 0.5 kB. These fragments are preferably fragments from an ε-subunit promoter comprising a nucleotide sequence shown in SEQ ID NO. 3. Particularly preferred 5' flanking sequence are fragments of an ε-promoter gene that is the human ε-promoter, or the rat ε-promoter, such as SEQ ID NO:3.

Also within the scope of the invention are regulatory elements which control tissue-specific expression of a gene and are functional equivalents or fragments or modified forms of the regulatory elements set forth above. Regulatory elements which are homologous to the regulatory elements set forth herein and which are capable of directing tissue-specific expression of a gene are also within the scope of the invention. Such functional equivalents and homologs are intended to include nucleic acid molecules which share sequence similarity to a sequence of SEQ ID NO:3. Preferred modifications of an ε-promoter region include those affecting nucleotides outside of promoters and enhancers as defined herein. A person of ordinary skill in the art would know that portions of such regulatory elements can be modified by nucleotide substitution, addition or deletion while the desired functionality is maintained. Furthermore, the methods invented herein provide numerous assays that can be performed to confirm that a functional equivalent or homolog of an ε-subunit regulatory element, is capable of regulating synapse-specific expression of a gene to which it is operably linked. Examples of these assays are set forth in the Example herein or are known in the art.

An ε-subunit regulatory element from a species other than rat or human can be used in the invention so long as it is capable of appropriately controlling expression of the heterologous gene to which it is operably linked. The ε-subunit can be isolated by methods known in the art, e.g. at hybridizations using stringent conditions. A preferred regulatory element for inducing expression of foreign gene in muscle cells at the NMJ is a fragment of a 5' flanking sequence ε-promoter gene including from about nucleotide −1 to about nucleotide −100 of the 5' flanking sequence, and comprising as the rat ε-subunit promoter having SEQ ID NO. 3. Another preferred fragment includes from about nucleotide −1 to about nucleotide −70 of a 5' flanking sequence of an ε-subunit gene, and such as comprising a sequence of SEQ ID NO. 3.

In one embodiment, the nucleic acid of the invention comprises at least two regulatory elements, such as two of the same or different promoters. For example, the regulatory element can include all or a portion of a human ε-subunit promoter or all or a portion of a rat ε-subunit promoter.

Also within the scope of the invention are constructs containing both 5' flanking and 3' flanking sequences from an ε-subunit gene operably linked to foreign gene.

Numerous assays can be performed to confirm that a promoter or a regulatory element is capable of controlling the expression of an operably linked exogenous gene in the desired tissue, e.g., muscle. For example, a fragment of a regulatory element, such as a sequence of an ε-subunit promoter, can be fused to a reporter gene, such as the gene encoding the chloramphenicol acetyl transferase gene (CAT), the gene for β-galactosidase, or the gene for luciferase. Preparation of these constructs and introduction into cells can be performed according to standard techniques. For this assay, it is desirable to transfect cell lines with the construct, that is cells or cell lines in which expression is desired or other cells or cell lines in which expression is not desired.

Another assay for determining the activity of a regulatory element is transfection of the regulatory element operably linked to a reporter gene into a cell line that is capable of differentiating in vivo. In this assay, the cell differentiates into a cell in which expression of the exogenous gene is desired. For example, embryonic muscle progenitors from rat embryos can be maintained under protocols that employ different concentrations of serum, and in the presence or absence of effectors such as a neuregulin, for example heregulin or ARIA, and inhibitors such as tetrodotoxin. When these muscle cells contain a reporter gene under the control of the ε-subunit promoter, the reporter gene is expressed concomitant with the differentiation of the embryonic cells into mature myotubes. Progenitor cells capable of differentiating into various types of cells upon being submitted to the proper conditions have also been established as stable cell lines, and are available from biological depositories such as the American Type Culture Collection.

An assay used to confirm cell studies of expression is to determine nuclear and cell response to plasmids injected to the muscles of an animal in vivo. Expression of appropriate linked reporter genes, and subcellular location of said expression, can be determined at the nuclear level after sacrifice of the animal.

Alternatively, the transcriptional activity of a regulatory element can be assayed by preparing transgenic mice containing the specific element as the transgene. Transgenic mice can be prepared according to methods known in the art and which are described in Leder et al. (U.S. Pat. No. 4,736,866). Expression of the foreign gene in the expected tissues of the transgenic mouse will indicate that the regulatory element is functionally active and can be used in the methods of the invention.

Following transfection of the muscle cells with the desired gene and regulatory elements together or not with a selection marker and selection, if appropriate, and demonstration that the desired gene is expressed in at least some cells, the cells can be administered to a subject.

Pharmaceutical Compositions

The Examples below are not intended as delimiting with respect to the nature of the nucleic acids, proteins or drugs, or to a particular route of the administration and additional routes are listed herein. In another embodiment of the present invention, the nucleic acids or drugs compositions of the invention can be administered by combination therapy, i.e., combined with other agents. For example, the combination therapy can include a composition of the present invention with at least one other nucleic acid or drug, at least one antibiotic, or other conventional therapy.

As used herein, "pharmaceutically acceptable carrier" includes any and all solvents, dispersion media, coatings, antibacterial and antifungal agents, isotonic and absorption delaying agents, and the like that are physiologically compatible. The use of such media and agents for pharmaceutically active substances is well known in the art. Preferably, the carrier is suitable for oral, intravenous, intramuscular, subcutaneous, parenteral, spinal or epidermal administration (e.g., by injection or infusion). Depending on the route of administration, the active compound can be coated in a material to protect the compound from the action of acids and other natural conditions that can inactivate the compound.

The phrases "parenteral administration" and "administered parenterally" as used herein means modes of administration other than oral and topical administration, usually by injection, and includes, without limitation, intravenous, intramuscular, intraarterial, intrathecal, intracapsular, intracardiac, intradermal, intraperitoneal, subcutaneous, subcuticular, intraarticular, subcapsular, subarachnoid, intraspinal, epidural and intrastemal injection and infusion.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation.

Transdermal patches offer the advantage of providing controlled delivery of a compound of the present therapeutic inventions to the body. Absorption enhancers can also be used to increase the flux of the composition across the skin. The rate of such flux can be controlled by either providing a rate controlling membrane or dispersing the composition in a polymer matrix or gel. Devices, including patches, which transdermally deliver a composition by iontophoresis or other electrically-assisted methods can also be employed in the present invention, including, for example, the devices described in U.S. Pat. Nos. 4,708,716 and 5,372,579.

One of ordinary skill in the art can determine and prescribe the effective amount of the pharmaceutical composition required. For example, one could start doses of the known or novel nucleic acid or drug levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be oral, intravenous, intramuscular, intraperitoneal, or subcutaneous. If administered proximal to the site of the target site of device implantation, then delivery routes other than oral and intravenous delivery are preferred. If desired, the effective daily dose of a therapeutic compositions can be administered as two, three, four, five, six or more sub-doses administered separately at appropriate intervals throughout the day, optionally, in unit dosage forms.

EXAMPLES

The invention is further illustrated by the following examples, which should not be construed as further limiting. The contents of all references, pending patent applications and published patents, cited throughout this application are hereby expressly incorporated by reference.

The following methodology described in the *Materials and Methods* section was used throughout these Examples, set forth below.

Materials and Methods

Cell Culture

Primary rat muscle cultures were prepared as described previously (Goldman, D., Carlson, B. M., and Staple, J. (1991) Neuron 7, 649–658). For experiments involving co-transfection with plasmid carrying a gene encoding a constitutively activated Ras, myotube cultures were harvested and used on day 5 after plating. For co-transfections with a plasmid encoding the dual specificity PTPase PTP CL100, fully differentiated myotube cultures harvested on day 6 after plating were used. The stable rat muscle L6 cells were grown in DMEM medium supplemented with 10% FCS. All cells were grown in 60 mm dishes.

Neuregulin

Recombinant neuregulin (GGF2; Cambridge Neuro-Science Inc., Cambridge, Mass.) was used at a final concentration of 5 nM.

Transfections

Cells were transfected by methods known in the art, for example, calcium phosphate co-precipitation as described (Sapru, M. K., Zhou, G., and Goldman, D. (1994) J. Biol. Chem. 269, 27811–27814).

For each plasmid transfection, the quantity of luciferase expressed from the regulated test plasmid was normalized to CAT expressed from the control plasmid, to control for efficiencies of transfections.

For PTPase overexpression studies, cells were transfected with 5 $\mu$g of test plasmid, 30 $\mu$g of plasmid PTP CL100 and 15–20 $\mu$g of plasmid CMV CAT. CMV CAT is not regulated by PTPase overexpression. Following a 1.5h incubation with DNA precipitate, the cells were glycerol-shocked for 90 seconds and placed in primary culture medium containing tetrodotoxin (2 $\mu$g/ml) and cytosine arabinoside (2.8 $\mu$g/ml).

For Ras expression studies, cells were transfected with 5–10 $\mu$g of plasmid carrying the gene for activated Ras, 20 $\mu$g of $\gamma$-722 CAT and 5 $\mu$g of test plasmid. $\gamma$-722 CAT is not regulated by Ras or neuregulin. At 12 h post-transfection, cells were placed in DMEM supplemented with 0.5% FCS for 48 h prior to harvesting for luciferase and CAT assays.

To study neuregulin-dependent regulation, L6 cells were transfected using 10 $\mu$g of test plasmid and 20 $\mu$g of $\gamma$-722 CAT. At 12 h post-transfection, the cells were washed with phosphate-buffered saline (PBS) and placed in differentiation medium (DMEM containing 2% horse serum). Cells were treated 24 hours later with neuregulin (5 nM), incubated for 60 h, and harvested and assayed for luciferase and CAT.

In Vivo Expression Assays

The in vivo expression assay involving direct injection of DNA into muscle has been described previously (Walke, W. et al. (1996) J. Neurosci. 16, 3641–3651; Duclert, A. et al.(1996) J. Biol. Chem. 271, 17433–17438; Koike, S. et al. (1995) Proc. Natl. Acad. Sci. USA 92, 10624–10628; 22). DNA preparations for direct injections were twice banded in a CsCl gradient, and resuspended in 0.15M NaCl at 4 mg/ml. Male Sprague Dawley rats, approximately 4 weeks old, were anaesthetized with ether, and small incisions through the skin were made above each of the right and left tibialis anterior (TA) muscle. Different syringes were used to inject 10 $\mu$l of DNA encoding wild-type or mutant $\epsilon$-promoter expression vector into the left or right TA muscle, respectively. Seven days after injection, animals were sacrificed, and left and right TA muscles were removed, fixed and stained for $\beta$-galactosidase activity (Sanes, J. R. et al. (1986) EMBO J. 5, 3133–3142Si, J.). Following staining, individual muscle fibers were teased apart under a dissecting microscope to identify blue fibers (those containing nuclear localized $\beta$-galactosidase activity). Blue fibers were then stained for acetylcholinesterase (Koelle, G. B., and Friedenwald, J. S. (1949) Proc. Soc. Biol. Med. 70, 617–622) to identify endplates. The number of blue fibers was scored and those containing blue nuclei centered beneath an endplate were scored as displaying synaptic expression, while all others were scored as displaying extra-synaptic expression. Each experiment used four animals, and was repeated at least four times.

Example 1

Construction of Expression Vectors

To localize the regulatory element that causes $\epsilon$-subunit to be expressed preferentially at the NMJ, 5' and 3' $\epsilon$-promoter deletions were introduced with exonuclease III, and the deletions obtained were subcloned into the pXP (Nordeen, S. K. (1988) BioTechniques 6, 454–457) vector for expression studies (FIG. 1). Deletion endpoints were determined by DNA sequencing. The pXP vector carries a luciferase reporter gene.

The mutant $\epsilon$-69 was subcloned upstream of the MEK (minimal enkephalin) promoter (Huggenvik, J. I. (1991) Molec. Endocrinol. 5:921–930) in pXP2 (Walke, W. et al (1996) J. Neurosci. 16, 3641–3651) because it showed little promoter activity on its own. The MEKpXP2 construct is not regulated by PTPase, neuregulin or Ras, so that the amount of $\epsilon$-69 contribution to overall promoter activity can be assessed by its ability to confer responsiveness to these agents.

The internal deletion, $\epsilon\Delta$-56/-67, was generated by subcloning a Nco1 and Kpn1 (blunted) fragment from $\epsilon 3'\Delta 65$ residing in plasmid BSSK (Stratagene Corp., LaJolla, Calif.) into the Nco1 and BspE1 (blunted) sites of $\epsilon$-2000 BSSK (Walke, W. et al. (1994) J. Biol. Chem. 269, 19447–19456).

Deletion endpoints were determined by DNA sequencing, and the mutation was then subcloned into Sma1 and Xho1 sites of pXP2 for expression studies.

ε-subunit promoter mutants εMUT1 and εMUT2 were created by PCR amplification using ε-2000 BSSK as a template. Since nucleotides -1 through -54 were dispensable for PTPase, neuregulin and Ras-dependent expression (FIG. 2), MUT1 and MUT2 oligonucleotide primers that were complementary to ε-subunit DNA were designed so that the amplified DNA's 3' end would reside at position -54. The M13 reverse sequencing primer was used to obtain hybridization upstream of the insert and result in an amplified product with a 5' end at position -2000. The MUT1 oligonucleotide sequence is 3' CCTAATCCACTGTCAGGGATTTGGAT-
CAAAATTTCGAATAT 5' (SEQ ID No. 1)

and the MUT2 sequence is

3' CCTAATCCACTGTCAGGGATTTCG-
GCTGGGCCTTCGAATAT 5' (SEQ ID No. 2).

These nucleotides span position -54 to -87 of the ε-subunit promoter and contain a Hind III site at their 3' end to facilitate subcloning. Mutants were confirmed by DNA sequencing, and the mutations were then subcloned into pXP2 for expression studies.

The activated Ras expression construct harbors a constitutively active (G12V) T24 H-ras-1 gene in the pSVgpt vector (Elizabeth, T. et al. (1982) Nature 300, 762–765).

The plasmid carrying the gene for the dual specificity PTPase, PTP CL100 (Sapru, M. K., et al. (1994) J Biol. Chem. 269, 27811–27814; Keyse, S. M., and Emslie, E. A. (1992) Nature 359, 644–647; Kwak, S. P. et al. (1994) J. Biol. Chem. 269, 3596–3604), was used as a prototype PTPase for overexpression studies.

The plasmid CMV CAT is described (See, for example, Sapru, M. K. et al. (1994) J Biol. Chem. 269, 27811–27814). The plasmid γ-722 CAT harbors a fragment of γ-subunit gene spanning nucleotides -754 to -33 (relative to the translation initiation site) regulating CAT expression (Gilmour, B. P. et al. (1991) J. Biol. Chem. 266, 19871–19874).

Expression constructs used in in vivo studies harbor either a wild-type (ε-2000) or a mutant (ε3'Δ65 or εMUT1) ε-subunit promoter regulating nuclear localized LacZ (nLacZ) expression.

Example 2

PTPase, Neuregulin and Ras-Dependent Control of ε-promoter Activity Map to a Common 15 bp Sequence Expression of the gene for nAChR ε-subunit can be suppressed by PTPase overexpression (Sapru, M. K. et al. (1994) J Biol. Chem. 269, 27811–27814) or induced by neuregulin (Martinou, J. C. et al. (1991) Proc. Natl. Acad. Sci. USA 88, 7669–7673). To identify DNA sequences in the rat ε-promoter that can mediate this regulation, a series of 5' and 3' deletion mutants was generated, which are schematically represented in FIG. 1.

Figure 2:
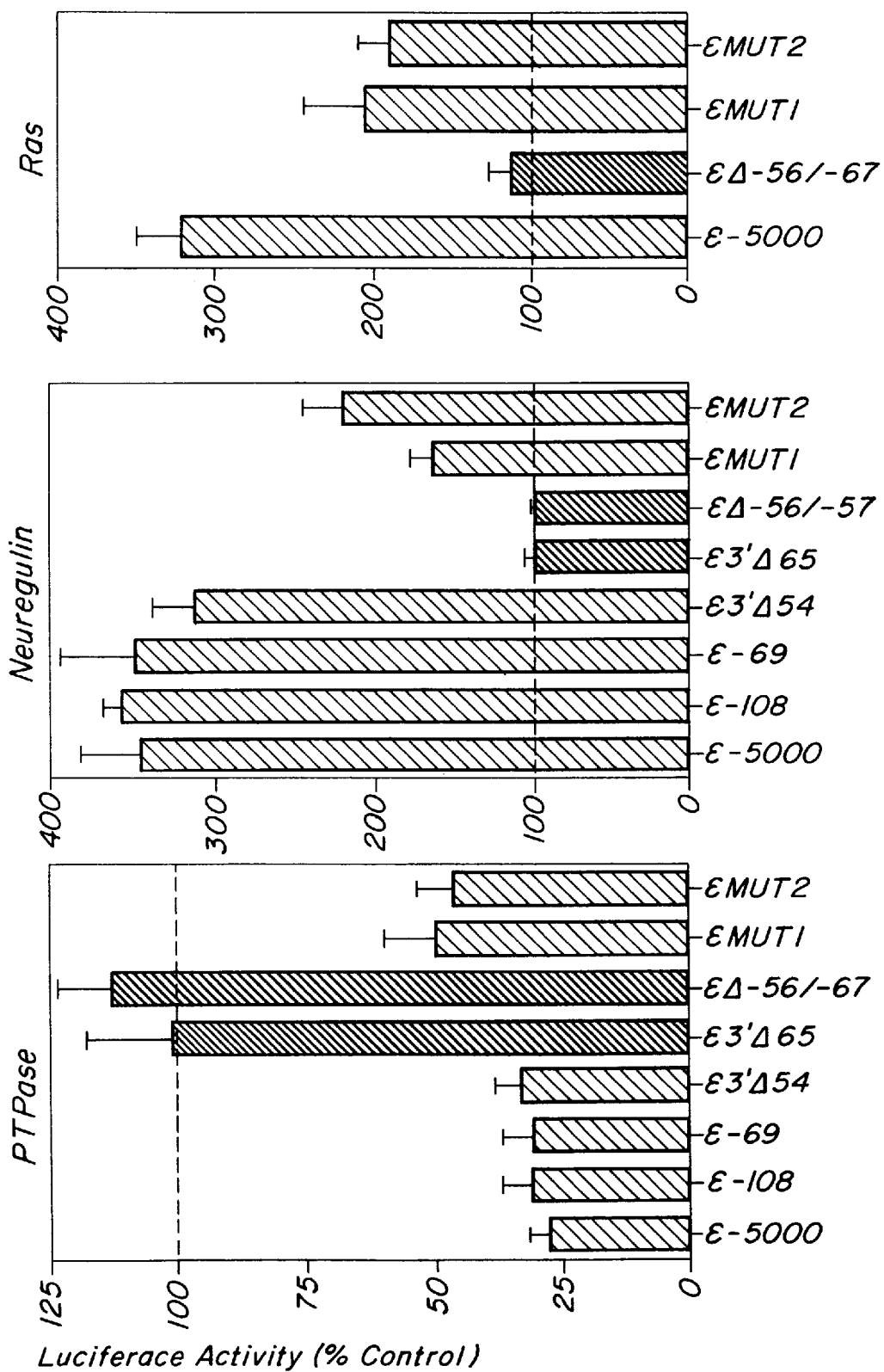
FIG. 2 is a bar graph that shows expression data used to identify the 15 bp sequence crucial for PTPase, neuregulin and Ras-dependent regulation of ε-subunit promoter activity. The left panel shows samples of primary rat myotube cultures, each co-transfected with the indicated ε-promoter/ luciferase expression vector described in FIG. 1, and with CMV CAT (for normalization for efficiency of transfection), in the presence and absence of PTP CL100. Cells were harvested 24 h post-transfection for luciferase and CAT assays. The middle panel shows data from samples of L6 stable rat muscle cells, each co-transfected with the indicated ε-promoter/luciferase expression vector and γ–722 CAT (for normalization for efficiency of transfection). After 24 h from the time of induction of differentiation, cells were treated with buffer or recombinant neuregulin (5 nM) for 60 h prior to harvesting, and assayed for luciferase and chloramphenicol acetyltransferase (CAT) activities. The right panel shows primary myotube cultures co-transfected with the indicated ε-promoter/luciferase expression vector, γ–722 CAT (for normalization for efficiency of transfection), in the presence and absence of activated-Ras. Cells were maintained in low serum medium (Dulbeco's Modified Eagle Medium, DMEM, with 0.5% fetal calf serum, FCS) for 48 h, and were to harvested and assayed for luciferase and CAT expression. Experiments were repeated at least three times. Bar graphs represent the average of triplicate transfections normalized to CAT activity; error bars represent the average plus and minus the standard deviation from the experimental data. Dotted line indicates control expression levels. Data are presented as a percentage of control.

Analysis of expression programmed by ε-promoter 5' and 3' deletion mutants was used to identify a PTPase and neuregulin responsive element. This element is here located as being downstream of nucleotide -69 and upstream of nucleotide -54 (FIG. 2, left and middle panels). For example, the internal deletion mutant, εΔ-56/-67, revealed that nucleotides -67 through -56 are essential for conferring this regulation (FIG. 2, left and middle panels). Lack of these nucleotides allowed 100% luciferase expression even in the presence of PTPase, and failed to induce luciferase in the presence of neuregulin.

Site-directed mutagenesis of nucleotides -59 through -56 (εMUT1) or -63 through -60 (εMUT2), was used to generate mutations in those essential nucleotides. The result of these mutations is that each of them caused partial loss of PTPase and neuregulin-dependent regulation (FIG. 2), and retained about half of the modulatory function. This shows that each of the two affected portions, from nucleotide -59 to -56, and from nucleotide -63 to -60, plays a role modulating transcription in response to PTPase and to neuregulin. It also shows that mutation of at least four of the base pairs of this region enables some function to be retained.

In stark contrast, deletion of 65 nucleotides from the 3' end of the promoter or deletion of nucleotides -67 through -56 resulted in complete loss of both PTPase and neuregulin-dependent expression (ε3'Δ65 and εΔ-56/-67 in FIG. 2). These surprising results demonstrate a crucial role for the 15 bp DNA sequence (positioned between -69 and -55) as the site of both PTPase and neuregulin-dependent regulation of ε-promoter activity. The sequence of this 15-b regions is 5' TAAACCTAGTCCGGA 3' (SEQ ID No. 3). This 15 bp sequence is thereby identified as the neuregulin responsive element (NRE) of the rat nAChR ε-subunit promoter.

Neuregulin mediates its effects on ε-gene expression via a Ras/MAP kinase pathway (Tansey, M. G. et al. (1996) J. Cell Biol. 134, 465–476; Si, J. et al. (1996) J. Biol. Chem. 271, 19752–19759). As shown herein, reporter gene expression under control of mutants with deletions ε3'Δ65 or εΔ-56/-67 was unresponsive to neuregulin (FIG. 2, middle panel), and hence might be unresponsive to activation by Ras. Indeed, the presence of activated Ras protein had no effect on the reporter gene expression downstream of deletions ε3=Δ65 and εΔ-56/-67, yet it caused more than a 300% increase in expression of reporter under control of wild-type ε-5000 (FIG. 2, right panel). Other data showed that Ras-dependent regulation of deletion mutants ε-69 and ε3'Δ54 was similar to that of ε-5000. In addition, like the effect observed with neuregulin-dependent expression, the promoter mutants εMUT1 and εMUT2 showed a partial loss of Ras-responsiveness (FIG. 2). The data from εMUT1 and εMUT2 show that the sequence of the four nucleotides at each end of the NRE identified here play some role in modulating the function of the NRE.

Mutant ε-108 had less promoter activity than the full length construct (Walke, Wet al. (1994) J. Biol. Chem. 269, 19447–19456). However, promoter mutations εΔ-56/-67, εMUT1, εMUT2 and the 3' deletion mutations exhibited an increase in promoter activity (values presented below), indicating that an effect of these deletions is the removal of at least one or several negative elements.

The values of the normalized luciferase activities for each of the various constructs, in the absence of co-transfection with a PTPase expression vector (control), were as follows:

ε-5000=207 (±14.6), ε-108=22 (±3), ε-69=477 (±87), ε3'Δ54=949 (±187), ε3'Δ65=1165 (±82), εΔ-56/-67=1090 (±144), εMUT1=639 (±68) and εMUT2=1042 (±63). Normalized luciferase activity for various constructs, in the absence of treatment with neuregulin (control), were as follows: ε-5000=7778 (±1070), ε-108=481 (±29), ε-69= 2517 (±162), ε3'Δ54=11057 (±961), ε3'Δ65=36451 (±6110), εΔ−56/−67=22076 (±1557), εMUT1=16472 (±2499) and εMUT2=18273 (±3677). Normalized luciferase activities for various promoter constructs, in the absence of co-transfection with Ras expression vector (control), were as follows: ε−5000=835 (±76), εΔ−56/−67=1370 (205), ε3'Δ65=1931 (±314), εMUT1=1368 (±31) and εMUT2=2044 (±115).

Example 3

In Vivo Expression from ε-Promoter

The results herein identified a 15 bp sequence crucial for PTPase, neuregulin and Ras-dependent regulation of ε-subunit promoter activity. This DNA element includes at its 3' end, the sequence CCGGA, which was recently shown to be necessary for synapse-specific expression of the mouse ε-subunit gene in vivo (Duclert, A. et al (1996) J. Biol. Chem. 271, 17433–17438). The data herein would suggest the 15 bp sequence of SEQ ID No. 3, is both necessary and sufficient, and has a greater effect on synapse-specific expression than CCGGA alone.

Figure 3:
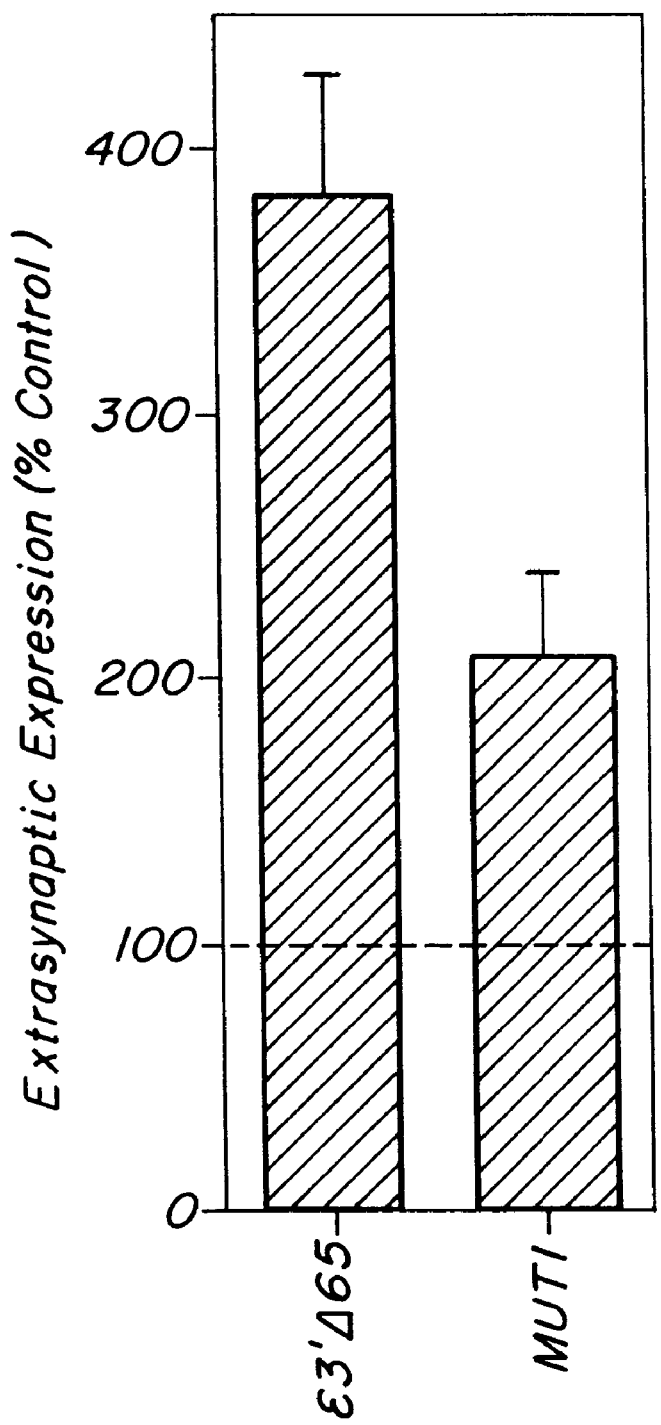
FIG. 3 is a bar graph that shows increased extrasynaptic expression in rat anterior tibialis muscle in vivo. Extrasynaptic expression of the wild-type ε-promoter construct ε–2000 nLacZ, the 3' deletion mutant ε3'Δ65, and the Ets binding site mutant, εMUT1, was examined using direct injection of DNA into muscle as described under experimental procedures; data are presented as mean values (percent of control ε–2000 nLacZ) plus and minus one standard error of mean; dotted line indicates the control expression levels; basal extrasynaptic expression for wild-type promoter expression vector was 5.66 (±0.86).

To further evaluate the role of the 5' flanking sequence, in vivo expression in rat thigh muscle, of wild-type ε−5000 nLacZ was compared with that of mutants ε3'Δ65 nLacZ and εMUT1 nLacZ. Mutants ε3'Δ65 nLacZ and εMUT1 nLacZ resulted in a 380% and 200% induction in extrasynaptic expression, respectively, compared to the wild-type construct (FIG. 3). These results indicate that the 15 bp sequence shown herein to be essential for mediating PTPase, neuregulin and Ras-dependent expression, contributes also to synapse-specific expression of the of ε-subunit gene in vivo by decreasing extrasynaptic expression.

The 15 bp DNA sequence (between positions −69 and −55; SEQ ID No. 3) in the rat nAChR ε-subunit gene contains nucleotides that are required for regulation by PTPase, neuregulin and Ras. Assays of in vivo expression show that this sequence also participates in extrajunctional suppression of the ε-subunit gene. Thus, this sequence functions as a positive element at the neuromuscular synapse increasing expression in response to neuregulin, and as a negative element maintaining low levels of ε-gene expression extrajunctionally elsewhere in the muscle fiber.

Example 4

Effect of Adjacent Nucleotides Proximal 5' to a Core Ets Binding Site Sequence

Neuregulin causes protein tyrosine phosphorylation of its receptors (Martinou, J. C., et al. (1991) Proc. Natl. Acad. Sci. USA 88, 7669–7673; Marchionni, M. A., et al. (1993) Nature 362, 312–317; Jo, S. A., et al. (1995) Nature 373, 158–161), and these receptors may be targets of overexpression of certain PTPases. Neuregulin also activates a Ras/MAP kinase signaling cascade (Tansey, M. G., et al. (1996) J. Cell Biol. 134, 465–476; Si, J. et al. (1996) J. Biol. Chem. 271, 19752–19759). Several MAP kinases are specific targets for inactivation by one or more of a dual specificity phosphatases of the CL100 family (Muda, M., et al. (1996) J. Biol. Chem. 271, 27205–27208). If PTPase mediated the effect observed herein by decreasing the activity of one or more neuregulin signaling components, the basal level of signaling in these cells, i.e., that level found in the absence of exogenous neuregulin, would be observed. Indeed, differentiated muscle cell cultures express neuregulin ( Moscoso, L. M., et al. (1995) Develop. Biol. 172, 158–169) which may activate a neuregulin-dependent signaling cascade. Therefore, PTPase overexpression can mediate its effects on ε-promoter activity by blocking this signaling cascade. PTPase overexpression can also act on a neuregulin independent signaling cascade that converges on the 15 bp DNA element described herein that mediates neuregulin responsiveness.

PTPase and neuregulin-responsiveness are mediated as described here by the 15 bp DNA sequence (SEQ ID No.:3) in the ε-subunit gene promoter, however, other PTPase-responsive elements that share some sequence identity can be responsive to neuregulin. A 104 bp fragment of the chick a-subunit promoter may harbor such an element. The neuregulin responsive 15 bp sequence of the rat ε-promoter defined herein contains, at positions −60 to −55, the sequence TCCGGA, which is an inverted repeat of the core Ets binding site sequence, GGA (Wasylyk, B. et al (1993) Eur. J. Biochem. 211, 7–18; Nye, J. A. et al. (1992) Genes & Development 6, 975–990). Neuregulin activates MAP kinase activity (Tansey, M. G. et al. (1996) J. Cell Biol. 134, 465–476; Si, J. et al. (1996) J. Biol. Chem. 271, 19752–19759). Ets proteins comprise a family of MAP kinase responsive transcription factors (Janknecht, R. et al. (1995) Oncogene 10, 1209–1216; Janknecht, R. (1996) Mol. and Cell. Biol. 16, 1550–1556; Marais, R. et al. (1993) Cell 73, 381–393; Rebay, I. and Rubin, G. (1995) Cell 81, 857–866).

One or more protein of the Ets transcription factor class can participate in neuregulin-dependent gene induction. Site directed mutagenesis described herein of the Ets-like binding site or sequences just upstream (εMUT1 and εMUT2, FIG. 2) reduced neuregulin-responsiveness only partially. Deletion of nucleotides −67 through −56 (spanning the putative Ets binding site and 5' flanking DNA) resulted in complete loss of neuregulin responsiveness (FIG. 2). Thus, while the putative Ets binding site is important for PTPase and neuregulin responsiveness, adjacent 5' sequences contribute also to the full level of this regulation. This conclusion is further supported by the data showing that in vivo, εMUT1 results in a 2-fold increase, while s 3'_65 results in a 4-fold increase in extrajunctional expression, compared to expression from the wild-type promoter (FIG. 3). These data show that the 15 bp sequence (SEQ ID No. 3), and not merely an Ets binding site, regulates both expression increases at the NMJ, and extrajunctional suppression of expression.

Example 5

Effect of Additional Distal 5' Flanking Sequences Further Upstream in the Rat ε-Promoter, and Independent Action of Ets Binding Sties DNA sequences participating in synapse-specific expression of the mouse δ- and ε-subunit genes have been identified (Duclert, A. et al. (1996) J. Biol. Chem. 271, 17433–17438; Koike, S. et al. (1995) Proc. Natl. Acad. Sci. USA 92, 10624–10628; 22), particularly, an N-box (CCGGAA) that is crucial for synapse-specific expression. The N-box harbors the putative Ets binding site core sequence GGA.

An Ets binding site (N box) mutant was created in mutant ε−154. The effect of this mutation reduced expression below the limits of detection in in vivo injection assays. Thus 5' sequences both at and upstream of nucleotide −154 participate in extrajunctional expression. These results indicated that the mouse 2.2 kb ε-promoter exhibits more pronounced synapse-specific expression than a promoter construct containing only 83 bp of 5' flanking DNA (Duclert, A et al. (1993) Proc. Natl. Acad. Sci. USA 90, 3043–3047). As shown herein, DNA located 5' of the putative rat Ets binding site influences synaptic expression of the ε-promoter. Ets proteins interact with other transcriptional regulators that bind sequences near the Ets binding site (Moscoso, L. M. et al. (1995) Develop. Biol. 172, 158–169). Inspection of rat ε-promoter sequences −69 to −55 that comprise sequence determinants for synapse-specific expression, identified two nucleotides that differ between rat and mouse (TAAACCTAGTCCGGA, SEQ ID No.:3, in rat compared to CAAACCTAGCCCGGA (SEQ ID NO:10), in mouse; interspecific differences underlined).

Differences in responses of various gene promoters to neuregulin, among the various nAChR subunit encoding genes, reflect the presence in these promoters of various alterations on the basic neuregulin responsive element in comparison to the one identified here (SEQ ID No. 3), and their precise activities which is a function of these sequences and the endogenous specific proteins that recognize and bind these sequences. Except for the putative Ets binding site, there is little conservation of sequence between the ε-subunit gene sequences −69 to −55 and the sequences of other nAChR subunit genes (α, β, γ and δ) expressed at the synapse. This is a function of respective differences in extent of activation of each of these genes by neuregulin, of which the ε-gene appears to be most responsive (Martinou, J. C., Falls, D. L., Fischbach, G. D., and Merlie, J. P. (1991) Proc. Natl. Acad. Sci. USA 88, 7669–7673). Further, presence of a putative Ets-binding site sequence does not necessarily confer neuregulin or PTPase-dependent expression since ε3'Δ65 retains an upstream putative Ets binding site sequence 5' CCGGAA 3' in reverse (centered around position −1368), yet is not regulated by addition of neuregulin or PTPase overexpression (FIG. 2).

Example 6

Cloning of a Rat Transcription Factor from a Lambda Library of Rat Hindlimb Muscle A variety of transcription factors related to the v-ets oncogene have been isolated from organisms encompassing flies to humans, and have been shown to be transcriptional activators (Wasylyk, B. et al., (1993) Eur. J. Biochem. 211:7–18). The core 5 bp consensus sequence recognized and bound by proteins of the Ets family is: C/T GGA A/T, where the term C/T indicates that both C and T are represented in the sequences analyzed to identify a consensus. In the present invention, the 15-bp NRE identified from the rat nAChR (-subunit promoter includes the sequence CGGA at the 3' end, hence the mouse Ets-2 protein was identified as a candidate transcriptional activator for this promoter. When a gene encoding mouse Ets-2 was co-transfected into muscle cells with a vector encoding rat NRE fused to a luciferase reporter gene, such that an increase in luciferase expression would indicate enhanced transcription, little or no enhancement was observed.

These data indicate that an endogenous transcription factor, not identical to mouse Ets-2 protein in a function such as DNA recognition or transcription activation, might mediate the effects of transcriptional regulation at NRE. To obtain such a protein, a bacteriophage (library of cDNA prepared from denervated rat lower hindlimb muscle tissue was plated in soft agar lawns with *Escherichia coli* host cells by standard methods known to one of ordinary skill in the art, to obtain $5 \times 10^5$ plaques. Each plate with plaques was blotted on filter papers, which were used to identify plaques with appropriate clones by probing with radiolabeled primers carrying the mouse Ets-2 sequence. Six plaques identified in this manner were purified, and further analyzed by determination of the DNA sequence of the inserted DNA.

All six of the plaques were found to carry cDNA of the same gene to different extents, some having only a partial sequence compared to others, and others carrying additional 3' untranslated regions with alternative splicing patterns. The longest clone was used to generate the full rat Ets-2 protein sequence, which is shown in FIG. 4 (SEQ ID No. 4).

Example 7

The Ets-2 Gene from Rat

Features of the protein shown using the standard one-letter system to indicate the amino acids (see, for example, New England Biolabs catalog, Beverly, Mass., for this system), that are shared with Ets family transcription factors, can be seen in FIG. 4 (SEQ ID No. 4). The members of this family have tryptophan repeats and a predominance of basic residues in the DNA binding domain. The rat Ets-2 protein has tryptophan residues (W) at positions 367, 385, and 404, as shown in FIG. 4, and basic residues arginine and lysine (R and K) for example at R-402, K-406, -410, -412, -417, R-420, -423, K-428, -433, -437, R-438, and R-442. Further, a nuclear localization signal identical to that of the Ets family consensus is found at residues 405–412 (GKRKNKPK) (SEQ ID NO:11).

The rat Ets-2 sequence of the present invention is highly similar to that for mouse Ets-2 (Watson, D. K. et al., (1988) Proc. Natl. Acad. Sci. USA 85:7862–7866), being 2 residues longer, and having 23 residues of the aligned sequences different from that of mouse (FIG. 5, with the rat ETS-2 amino acid sequence shown above and that of the mouse shown below). The Ets-2 protein of mouse is 469 residues in length, and rat is 471. Two residues, E-234 and Q-235 of rat Ets-2, are not found in the mouse aligned sequence. Of the 23 non-identical residues, 22 are found in the N-terminal portion of the protein, which has been identified as the transcriptional activation domain (Wasylyk et al., referenced herein). The program used to align and compare these proteins as shown in Fig. % assigned a 95% identity score.

Example 8

Neuregulin Signaling is Mediated by Transcription Through Rat Ets-2 Protein

Transcription modulated in rat muscle L6 cells at the 15 bp NRE was assessed using the (5000-luciferase construct by assaying luciferase activity under each experimental condition. A deletion mutation of the rat Ets-2 gene was constructed by standard techniques of mutagenesis, removing N-terminal residues such that the portion of the gene encoding residues 355–471, the DNA-binding domain, of this protein were retained. This truncated rat Ets-2 gene was co-transfected into L6 cells carrying the NRE-luciferase fusion.

Figure 6:
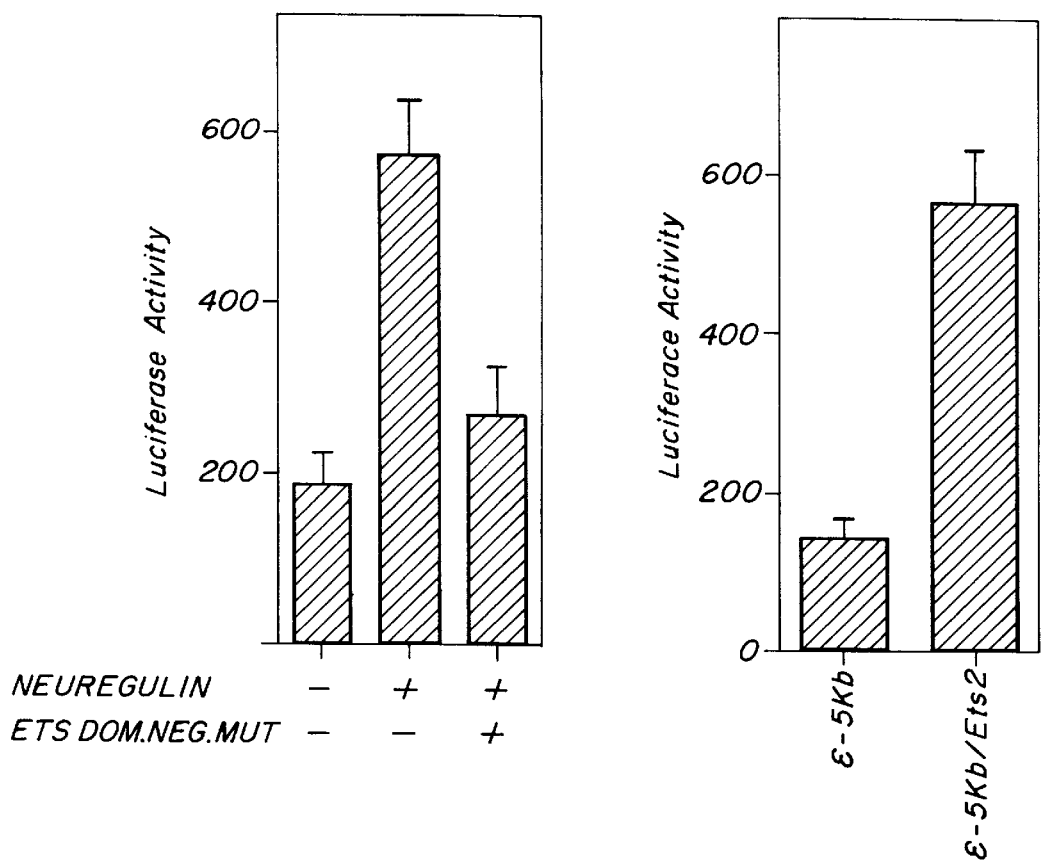
FIG. 6 is a bar graph representation of luciferase activity in rat muscle L6 cells transfected with the (5000 fusion construct harboring the 15-bp NRE of SEQ ID No. 3 linked to the luciferase reporter gene. The left panel shows the effect of addition of neuregulin to the cell medium, and the effect of co-transfection of cells with a construct harboring the truncated rat Ets-2 gene encoding residues 355–471, and lacking the transcription activation domain. The right panel shows the effect of co-transfection of cells with a construct harboring the gene for wild-type rat Ets-2.

Results shown in FIG. 6, left panel, indicate that the intracellular presence of the truncated DNA-binding Ets-2 protein has a negative and dominant effect on neuregulin induction of transcription phenotype. Control cells not transfected with the truncated Ets-2 gene display almost a three-fold transcriptional induction of luciferase reporter activity after addition of neuregulin to the medium. The presence of the truncated Ets-2 DNA binding domain, however, blocks most of the neuregulin induction, indicating that the truncated protein in binding the NRE and blocking activation of transcription of the luciferase gene downstream of the NRE.

The wild-type full-length rat Ets-2 gene, co-transfected with the NRE-luciferase construct, however, stimulates transcriptional induction (FIG. 6, right panel), in comparison to cells transfected only with the reporting construct. The basal level of luciferase is presumably due to the presence of endogenous cellular Ets-2 and endogenous neuregulin.

Equivalents

Those skilled in the art will recognize, or be able to ascertain using no more than routine experimentation, many equivalents to the specific embodiments of the invention described herein. Such equivalents are intended to be encompassed by the following claims.

---

What is claimed is:

1. An isolated nucleic acid comprising a neuregulin response element derived from a contiguous promoter sequence existing in a naturally occurring genome of an organism, wherein said neuregulin response element is operably linked to and regulates a heterologous gene, wherein the neuregulin response element comprises a nucleic acid sequence as shown in SEQ ID No.:3.

2. A neuregulin response element comprising an isolated nucleic acid which differs in sequence from all or a portion of that of SEQ ID No. 3 by four or fewer nucleotides, and is capable of modulating expression of an operably linked gene under the regulation of a protein selected from the group consisting of the neuregulin family, an activated Ras protein, and a dual specificity protein phosphatase.

3. The isolated nucleic acid of either claim 1 or claim 2, wherein the ability of the neuregulin response element to regulate a heterologous gene to which it is operably linked is modulated by an agent which stimulates the mitogen activated protein (MAP) kinase signaling pathway.

4. The isolated nucleic acid of either claim 1 or claim 2, wherein the ability of the neuregulin response element to regulate the heterologous gene is modulated by an agent selected from the group consisting of a protein of the neuregulin family, an activated Ras protein, and a dual specificity protein tyrosine phosphatase (PTPase).

5. A construct comprising a heterologous gene operably linked to the neuregulin response element of either claim 1 or claim 2 in an expression vector.

6. A host cell transfected with the construct of claim 5.

7. The host cell of claim 6 wherein the cell is selected from the group consisting of a worm cell, an insect cell, a fish cell, an avian cell and a mammalian cell.

8. The host cell of claim 6 wherein the cell is a nerve cell or a muscle cell.

* * * * *

SEQUENCE LISTING

<160> NUMBER OF SEQ ID NOS: 11

<210> SEQ ID NO 1
<211> LENGTH: 41
<212> TYPE: DNA
<213> ORGANISM: Rattus sp.

<400> SEQUENCE: 1
tataagcttt aaaactaggt ttagggactg tcacctaatc c          41

<210> SEQ ID NO 2
<211> LENGTH: 41
<212> TYPE: DNA
<213> ORGANISM: Rattus sp.

<400> SEQUENCE: 2
tataagcttc cgggtcgggt ttagggactg tcacctaatc c          41

<210> SEQ ID NO 3
<211> LENGTH: 15
<212> TYPE: DNA
<213> ORGANISM: Rattus sp.

<400> SEQUENCE: 3
taaacctagt ccgga          15

<210> SEQ ID NO 4
<211> LENGTH: 470
<212> TYPE: PRT
<213> ORGANISM: Rattus sp.

<400> SEQUENCE: 4

Met Asn Asp Phe Gly Ile Lys Asn Met Asp Gln Val Ala Pro Val Ala
 1               5                  10                  15

Asn Ser Phe Arg Gly Thr Leu Lys Arg Gln Pro Ala Phe Asp Thr Phe
            20                  25                  30

Asp Gly Ser Leu Phe Ala Val Leu Pro Ser Leu Ser Glu Glu Gln Thr
        35                  40                  45

Leu Gln Glu Val Pro Thr Gly Leu Asp Ser Val Ser His Asp Ser Ala
    50                  55                  60

Thr Cys Glu Leu Pro Leu Leu Thr Pro Cys Ser Lys Ala Val Met Ser
65                  70                  75                  80

Gln Ala Leu Lys Ala Thr Phe Ser Gly Phe His Lys Glu Gln Arg Arg
                85                  90                  95

Leu Gly Ile Pro Lys Asn Pro Trp Leu Trp Asn Glu Gln Val Cys
            100                 105                 110

Gln Trp Leu His Trp Ala Thr Asn Glu Phe Ser Leu Val Asn Val Asn
        115                 120                 125

Leu Gln Arg Phe Gly Met Asn Gly Gln Met Leu Cys Asn Leu Gly Lys
    130                 135                 140

```
Glu Arg Phe Leu Glu Leu Ala Pro Asp Phe Val Gly Asp Ile Leu Trp
145                 150                 155                 160

Glu His Leu Glu Gln Met Ile Lys Glu Asn Gln Glu Lys Thr Glu Asp
            165                 170                 175

Gln Tyr Glu Glu Asn Ser His Leu Asn Ala Val Pro His Trp Ile Asn
        180                 185                 190

Ser Asn Thr Leu Gly Phe Gly Val Glu Gln Ala Pro Tyr Gly Met Gln
    195                 200                 205

Ala Pro Ser Tyr Leu Lys Asp Gly Leu Leu Asp Gly Met Cys Pro Pro
210                 215                 220

Ser Ala Thr Pro Ala Ala Leu Gly Ser Glu Gln Glu Leu Gln Met Leu
225                 230                 235                 240

Pro Lys Ser Arg Leu Asn Thr Val Ser Val Asn Tyr Cys Ser Ile Ser
                245                 250                 255

Gln Asp Phe Pro Gly Gly Asn Leu Asn Leu Leu Asn Ser Ser Ser Gly
            260                 265                 270

Lys Pro Lys Glu His Asp Ser Pro Glu Asn Gly Gly Asp Ser Phe Glu
        275                 280                 285

Ser Ser Asp Ser Leu Leu Arg Ser Trp Asn Ser Gln Ser Ser Leu Leu
    290                 295                 300

Asp Val Gln Arg Val Pro Ser Phe Glu Ser Phe Glu Asp Cys Ser
305                 310                 315                 320

Gln Ser Leu Cys Leu Ser Lys Pro Thr Met Ser Phe Lys Asp Tyr Ile
                325                 330                 335

Gln Glu Arg Ser Asp Pro Val Glu Gln Gly Lys Pro Val Ile Pro Ala
            340                 345                 350

Ala Val Leu Ala Gly Phe Thr Gly Ser Gly Pro Ile Gln Leu Trp Gln
        355                 360                 365

Phe Leu Leu Glu Leu Leu Ser Asp Lys Ser Cys Gln Ser Phe Ile Ser
    370                 375                 380

Trp Thr Gly Asp Gly Trp Glu Phe Lys Leu Ala Asp Pro Asp Glu Val
385                 390                 395                 400

Ala Arg Arg Trp Gly Lys Arg Lys Asn Lys Pro Lys Met Asn Tyr Glu
                405                 410                 415

Lys Leu Ser Arg Gly Leu Arg Tyr Tyr Tyr Asp Lys Asn Ile Ile His
            420                 425                 430

Lys Thr Ser Gly Lys Arg Tyr Val Tyr Arg Phe Val Cys Asp Leu Gln
        435                 440                 445

Asn Leu Leu Gly Phe Thr Pro Glu Glu Leu His Ala Ile Leu Gly Val
    450                 455                 460

Gln Pro Asp Thr Glu Asp
465                 470
```

<210> SEQ ID NO 5
<211> LENGTH: 11
<212> TYPE: DNA
<213> ORGANISM: Rattus sp.

<400> SEQUENCE: 5
ctagtccgga a                                                          11

<210> SEQ ID NO 6
<211> LENGTH: 10
<212> TYPE: DNA
<213> ORGANISM: Rattus sp.

-continued

```
<400> SEQUENCE: 6
ctagtccgga                                                                10

<210> SEQ ID NO 7
<211> LENGTH: 11
<212> TYPE: DNA
<213> ORGANISM: Rattus sp.

<400> SEQUENCE: 7
ctagttttaa a                                                              11

<210> SEQ ID NO 8
<211> LENGTH: 11
<212> TYPE: DNA
<213> ORGANISM: Rattus sp.

<400> SEQUENCE: 8
ccgacccgga a                                                              11

<210> SEQ ID NO 9
<211> LENGTH: 468
<212> TYPE: PRT
<213> ORGANISM: Mus musculus

<400> SEQUENCE: 9
```

Met Asn Asp Phe Gly Ile Lys Asn Met Asp Gln Val Ala Pro Val Ala
1               5                   10                  15

Asn Ser Phe Arg Gly Thr Leu Lys Arg Gln Pro Ala Phe Asp Thr Phe
            20                  25                  30

Asp Gly Ser Leu Phe Ala Val Leu Pro Ser Leu Ser Glu Asp Gln Thr
        35                  40                  45

Leu Gln Glu Val Pro Thr Gly Leu Asp Ser Val Ser His Asp Ser Ala
    50                  55                  60

Ser Cys Glu Leu Pro Leu Leu Thr Pro Cys Ser Lys Ala Val Met Ser
65                  70                  75                  80

Gln Ala Leu Lys Ala Thr Phe Ser Gly Phe Gln Lys Glu Gln Arg Arg
                85                  90                  95

Leu Gly Ile Pro Lys Asn Pro Trp Leu Trp Ser Glu Gln Val Cys
            100                 105                 110

Gln Trp Leu Leu Trp Ala Thr Asn Glu Phe Ser Leu Val Asn Val Asn
        115                 120                 125

Leu His Gln Phe Gly Met Asn Gly Gln Met Leu Cys Asn Leu Gly Lys
    130                 135                 140

Glu Arg Phe Leu Glu Leu Ala Pro Asp Phe Val Gly Asp Ile Leu Trp
145                 150                 155                 160

Glu His Leu Glu Gln Met Ile Lys Glu Asn Gln Glu Lys Thr Glu Asp
                165                 170                 175

Gln Tyr Glu Glu Asn Ser His Leu Asn Ala Val Pro His Trp Ile Asn
            180                 185                 190

Ser Asn Thr Leu Gly Phe Ser Met Glu Gln Ala Pro Tyr Gly Met Gln
        195                 200                 205

Ala Pro Asn Tyr Pro Lys Asp Asn Leu Leu Asp Ser Met Cys Pro Pro
    210                 215                 220

Ser Ala Thr Pro Ala Ala Leu Gly Ser Glu Leu Gln Met Leu Pro Lys
225                 230                 235                 240

Ser Arg Leu Asn Thr Val Asn Val Asn Tyr Cys Ser Ile Ser Gln Asp

-continued

```
                         245                 250                 255
Phe Pro Ser Ser Asn Val Asn Leu Leu Asn Asn Asn Ser Gly Lys Pro
            260                 265                 270

Lys Asp His Asp Ser Pro Glu Asn Gly Gly Asp Ser Phe Glu Ser Ser
        275                 280                 285

Asp Ser Leu Leu Arg Ser Trp Asn Ser Gln Ser Ser Leu Leu Asp Val
    290                 295                 300

Gln Arg Val Pro Ser Phe Glu Ser Phe Glu Glu Asp Cys Ser Gln Ser
305                 310                 315                 320

Leu Cys Leu Ser Lys Leu Thr Met Ser Phe Lys Asp Tyr Ile Gln Glu
            325                 330                 335

Arg Ser Asp Pro Val Glu Gln Gly Lys Pro Val Ile Pro Ala Ala Val
            340                 345                 350

Leu Ala Gly Phe Thr Gly Ser Gly Pro Ile Gln Leu Trp Gln Phe Leu
            355                 360                 365

Leu Glu Leu Leu Ser Asp Lys Ser Cys Gln Ser Phe Ile Ser Trp Thr
    370                 375                 380

Gly Asp Gly Trp Glu Phe Lys Leu Ala Asp Pro Asp Glu Val Ala Arg
385                 390                 395                 400

Arg Trp Gly Lys Arg Lys Asn Lys Pro Lys Met Asn Tyr Glu Lys Leu
            405                 410                 415

Ser Arg Gly Leu Arg Tyr Tyr Tyr Asp Lys Asn Ile Ile His Lys Thr
            420                 425                 430

Ser Gly Lys Arg Tyr Val Tyr Arg Phe Val Cys Asp Leu Gln Asn Leu
            435                 440                 445

Leu Gly Phe Thr Pro Glu Glu Leu His Ala Ile Leu Gly Val Gln Pro
    450                 455                 460

Asp Thr Glu Asp
465

<210> SEQ ID NO 10
<211> LENGTH: 15
<212> TYPE: DNA
<213> ORGANISM: Rattus sp.

<400> SEQUENCE: 10
caaacctagc ccgga                                              15

<210> SEQ ID NO 11
<211> LENGTH: 8
<212> TYPE: PRT
<213> ORGANISM: Rattus sp.

<400> SEQUENCE: 11

Gly Lys Arg Lys Asn Lys Pro Lys
1               5
```